(12) United States Patent
El Sayed et al.

(10) Patent No.: US 10,945,983 B2
(45) Date of Patent: Mar. 16, 2021

(54) OLEOCANTHAL ISOLATION AND CANCER TREATMENT

(71) Applicant: Board of Supervisors for the University of Louisiana System, Monroe, LA (US)

(72) Inventors: Khalid A. El Sayed, West Monroe, LA (US); Abu Bakar Siddique, Monroe, LA (US); Hassan Y. Ebrahim, Cairo (EG)

(73) Assignee: BOARD OF SUPERVISORS FOR THE UNIVERSITY OF LOUISIA, Monroe, LA (US)

( * ) Notice: Subject to any disclaimer, the term of this patent is extended or adjusted under 35 U.S.C. 154(b) by 297 days.

(21) Appl. No.: 16/079,122

(22) PCT Filed: Jul. 21, 2017

(86) PCT No.: PCT/US2017/043308
§ 371 (c)(1),
(2) Date: Aug. 23, 2018

(87) PCT Pub. No.: WO2018/017967
PCT Pub. Date: Jan. 25, 2018

(65) Prior Publication Data
US 2019/0192469 A1 Jun. 27, 2019

Related U.S. Application Data

(60) Provisional application No. 62/365,148, filed on Jul. 21, 2016.

(51) Int. Cl.
| | | |
|---|---|---|
| *A61K 31/222* | (2006.01) | |
| *C07C 67/56* | (2006.01) | |
| *C07C 67/58* | (2006.01) | |
| *A61P 17/02* | (2006.01) | |
| *A61P 17/00* | (2006.01) | |
| *A61P 35/00* | (2006.01) | |
| *A61K 9/107* | (2006.01) | |
| *C07C 69/738* | (2006.01) | |

(52) U.S. Cl.
CPC ........... *A61K 31/222* (2013.01); *A61P 17/00* (2018.01); *A61P 17/02* (2018.01); *A61P 35/00* (2018.01); *C07C 67/56* (2013.01); *C07C 67/58* (2013.01); *A61K 9/1075* (2013.01); *C07C 69/738* (2013.01)

(58) Field of Classification Search
CPC ..... A61K 31/222; A61K 9/1075; A61P 17/02; A61P 17/00; A61P 35/00; C07C 67/56; C07C 67/58; C07C 69/738
See application file for complete search history.

(56) References Cited

U.S. PATENT DOCUMENTS

| | | |
|---|---|---|
| 5,104,587 A | 4/1992 | Besserman et al. |
| 6,284,904 B1 | 9/2001 | Ponnampalam |
| 2002/0054924 A1 | 5/2002 | Leahy et al. |
| 2009/0076142 A1 | 3/2009 | Han et al. |
| 2010/0160690 A1 | 6/2010 | Lopez Mas et al. |
| 2012/0045406 A1 | 2/2012 | Urban et al. |
| 2014/0088299 A1 | 3/2014 | Klapish et al. |

FOREIGN PATENT DOCUMENTS

| | | | |
|---|---|---|---|
| FR | 2 904 312 A1 | 2/2008 | |
| FR | 2904312 A1 * | 2/2008 | ............. C07C 67/58 |

OTHER PUBLICATIONS

Mohyeldin et al., "The Oleocanthal-based Homovanilyl Sinapate as a Novel c-Met Inhibitor", Apr. 11, 2016, Oncotarget, vol. 7, No. 22, pp. 32247-32273; p. 32248.
Hydoxytyrosol, Wikipedia, May 23, 2016, Retrieved on Sep. 12, 2017, https://en.wikipedia.org/wiki/hydroxytyrosol, 3 pages.
Olecanthal, Wikipedia, Jun. 4, 2016, Retrieved on Sep. 12, 2017, https://en.wikipedia.org/wiki/oleocanthal, 3 pages.
Polystyrene, Wikipedia, Jun. 30, 2016, Retrieved on Sep. 12, 2017, https://en.wikipedia.org/wiki/polystyrene, 14 pages.
Relite, Product Line—Adsorbent Resins, Resindion SRL, 2011; Retrieved on Sep. 12, 2017, https://www.resindion.com/index.php?option=com_content&view=article&id=113&itemid=122&jjj=1505246141826, 2 pages.
Polar Protic and Aprotic Solvents, Chemistry LibreTexts, Sep. 2, 2015, Retrieved on Sep. 12, 2017, https://chem.libretexts.org/core/organic_chemistry/fundamentals/intermolecular_forces/polar_protic_and_aprotic_solvents, 4 pages.
Sindana et al., "Recycle HPLC: A Powerful Tool for the Purification of Natural Products", Hindawi Publishing Corporation, Chromatography Research International, Oct. 2, 2013, vol. 2013, 8 pages.
International Search Report Corresponding to PCT/US2017/043308 dated Oct. 12, 2017, 3 pages.
Written Opinion Corresponding to PCT/US2017/043308 dated Oct. 12, 2017, 7 pages.
European Search Report issued in corresponding European Patent Application No. 17831964.6 dated Feb. 26, 2020.

\* cited by examiner

*Primary Examiner* — Aaron J Kosar
(74) *Attorney, Agent, or Firm* — Davis & Bujold PLLC; Charles G. Holoubek; Michael Bujold

(57) ABSTRACT

A method for extracting S (-)-Oleocanthal from olive oil comprising mixing a first volume of water with a second volume of olive oil to form an olive oil/water mixture; letting the olive oil/water mixture stand; removing an aqueous fraction from the olive oil/water mixture leaving a reduced S (-)-Oleocanthal containing olive oil; and filtering the aqueous fraction to create aqueous S (-)-Oleocanthal.

18 Claims, 36 Drawing Sheets

(-)-Oleocanthal

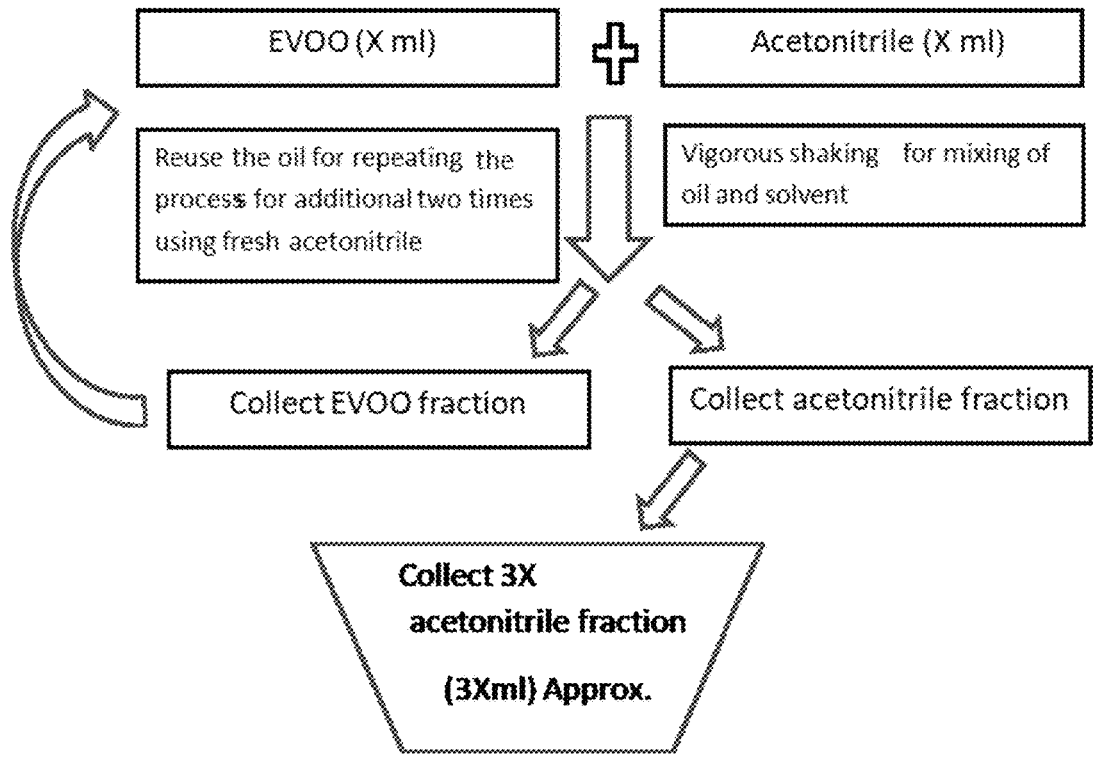
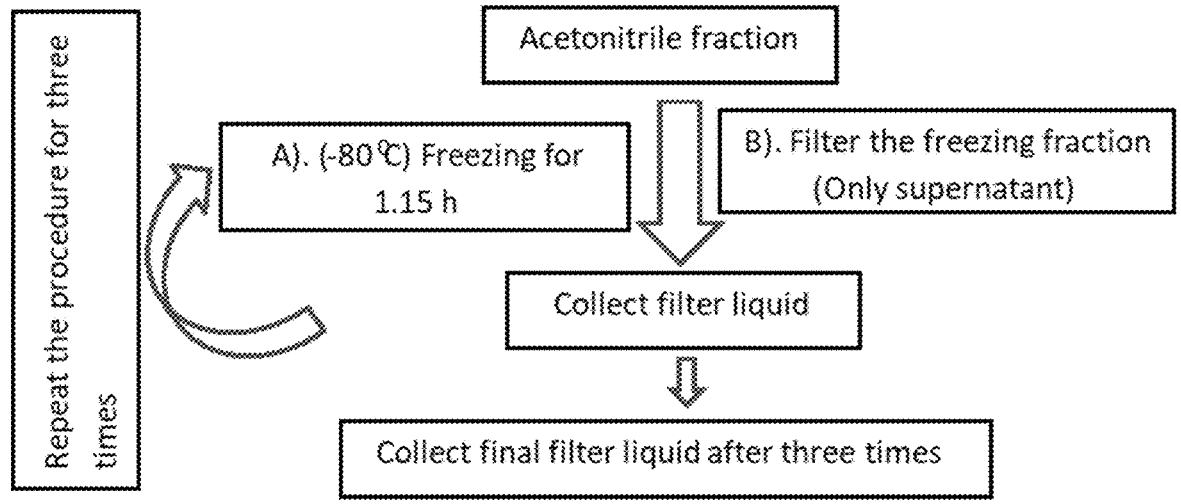
FIG. 3

(-)-Oleocanthal, Rγ=2.8mins

Oleocanthal Spot
Oleocanthal Spot

Standard Calibration Curve in HPLC
Area under the Peak
Y=40804x+112696
R2 = 0.999
Oleocanthal Conc. ug/ml Standard Calibration Curve
Integration Ratio
Y=0.0833x+0.0012
R2 = 0.9995
Oleocanthal Conc. mg/750ul

| Sample Code | Type of Oil | Batch No. | Source | Oleocanthal Qt. Before Ex. in EVOO (A) | Oleocanthal Qt. WE* (B) | Oleocanthal Qt. After Ex. in EVOO (C) | % of Recovery (B/A)*100 | **Pure Qt. (D) | % of Yield (D/A)*100 | One month stability for WE (E) RT (E) | One month stability % degradation 100-(E/B)*100 | One month stability for WE (E) 4°C (F) | % degradation 100-(F/B)*100 |
|---|---|---|---|---|---|---|---|---|---|---|---|---|---|
| SAMPLE 1 | EVOO | NA | Florida, USA | 87.38 | 87.09 | 1.00 | 98.88 | NP | NP | 3.18 | 96.34 | 13.34 | 84.67 |
| SAMPLE 2 | EVOO | NA | Florida, USA | 82.89 | 80.15 | 4.00 | 95.23 | NP | NP | 3.81 | 95.23 | 6.46 | 91.95 |
| SAMPLE 3 | EVOO | NA | Florida, USA | 14.15 | 10.81 | 1.89 | 73.35 | NP | NP | 0.00 | 100 | 4.07 | 62.35 |
| SAMPLE 4 | EVOO | NA | Florida, USA | 0.00 | 0.00 | NN | NN | NN | NN | NN | NN | NN | NN |
| SAMPLE 5 | Brodoichre Cold Press EVOO | L183TE-241 | Italy | 222.61 | 149.45 | 73.6 | 67.13 | 186.57 | 83.86 | 0.30 | 99.79 | 9.34 | 93.95 |
| SAMPLE 6 | Brodoichre Cold Press EVOO | L245TE-241 | Italy | 108.82 | 90.76 | 16.08 | 84.96 | NP | NP | 0.0 | 100 | 6.81 | 92.43 |
| SAMPLE 7 | EVOO | L022RE-566 | Italy | 98.4 | 96.85 | 1.55 | 98.42 | 83.10 | 85.80 | NP | NP | NP | NP |
| SAMPLE 8 | Corn Oil | NA | TX, USA | 0.00 | 0.00 | NN | NN | NN | NN | NN | NN | NN | NN |

FIG. 9

FIG. 21A
FIG. 21B
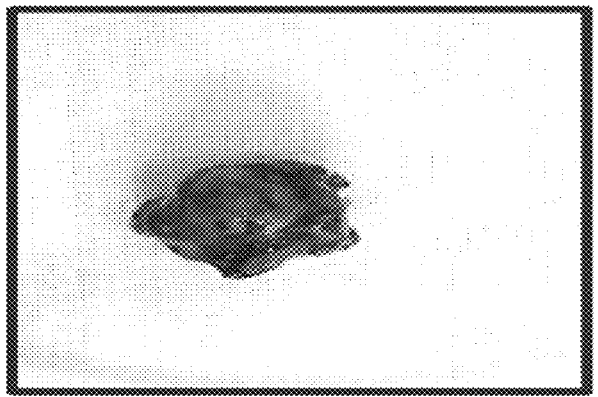
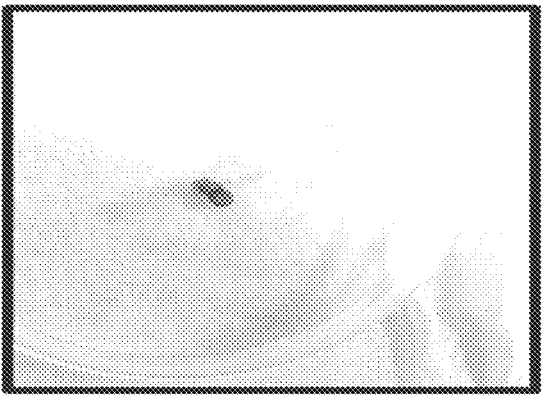
Vehicle Control          Oleocanthal

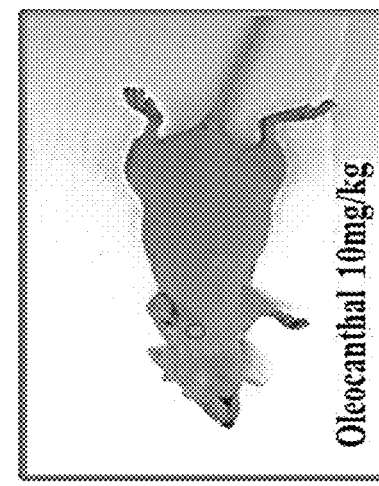
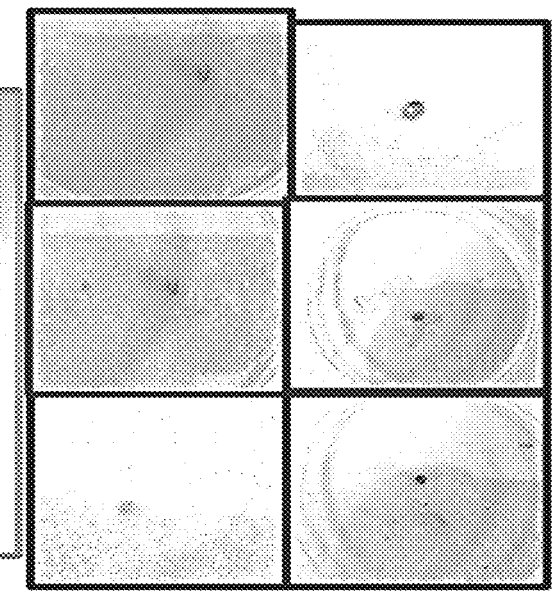
FIG. 28A
Vehicle Control
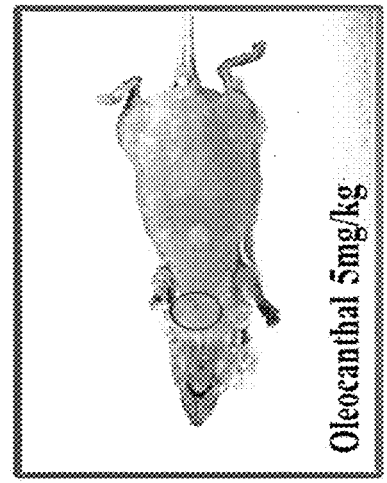
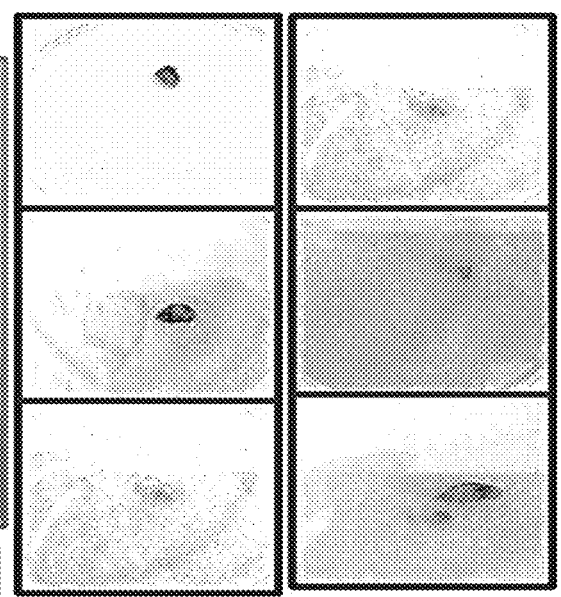
FIG. 28B
Oleocanthal 5mg/kg
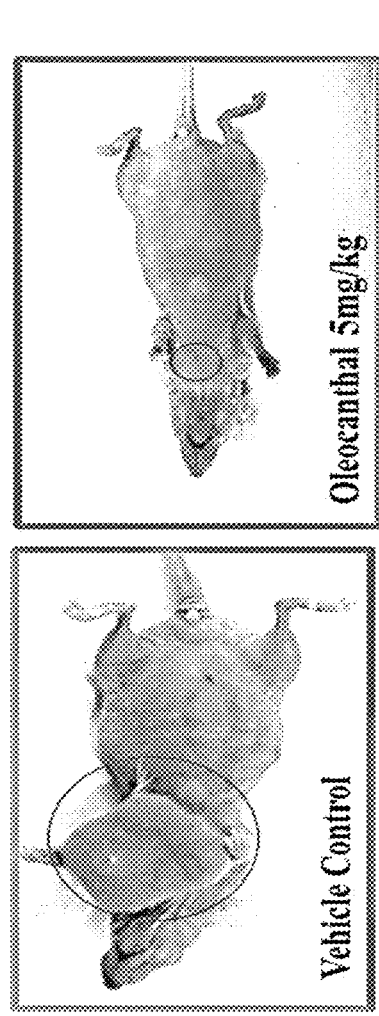
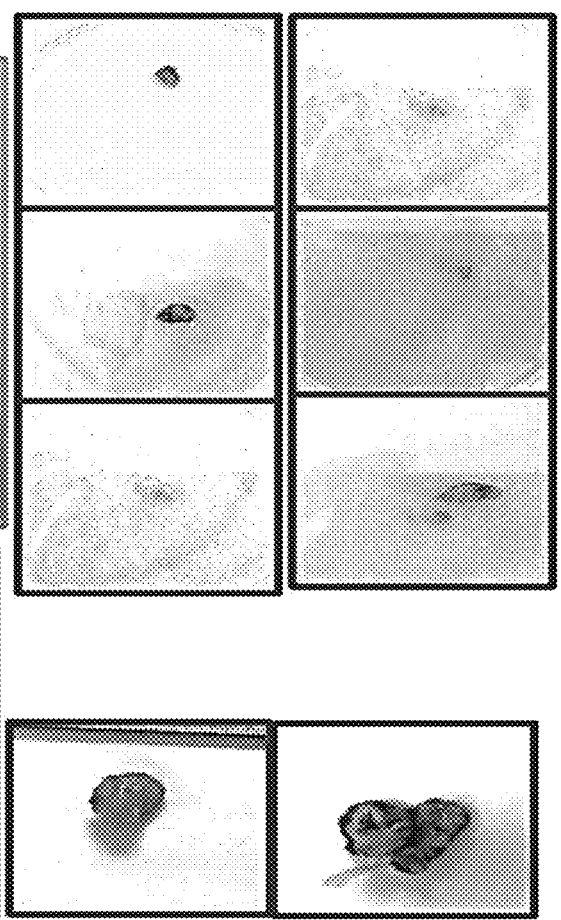
FIG. 28C
Oleocanthal 10mg/kg
Oleocanthal 5.0 mg/kg 3X/week, ip
Oleocanthal 10.0 mg/kg
Vehicle Control

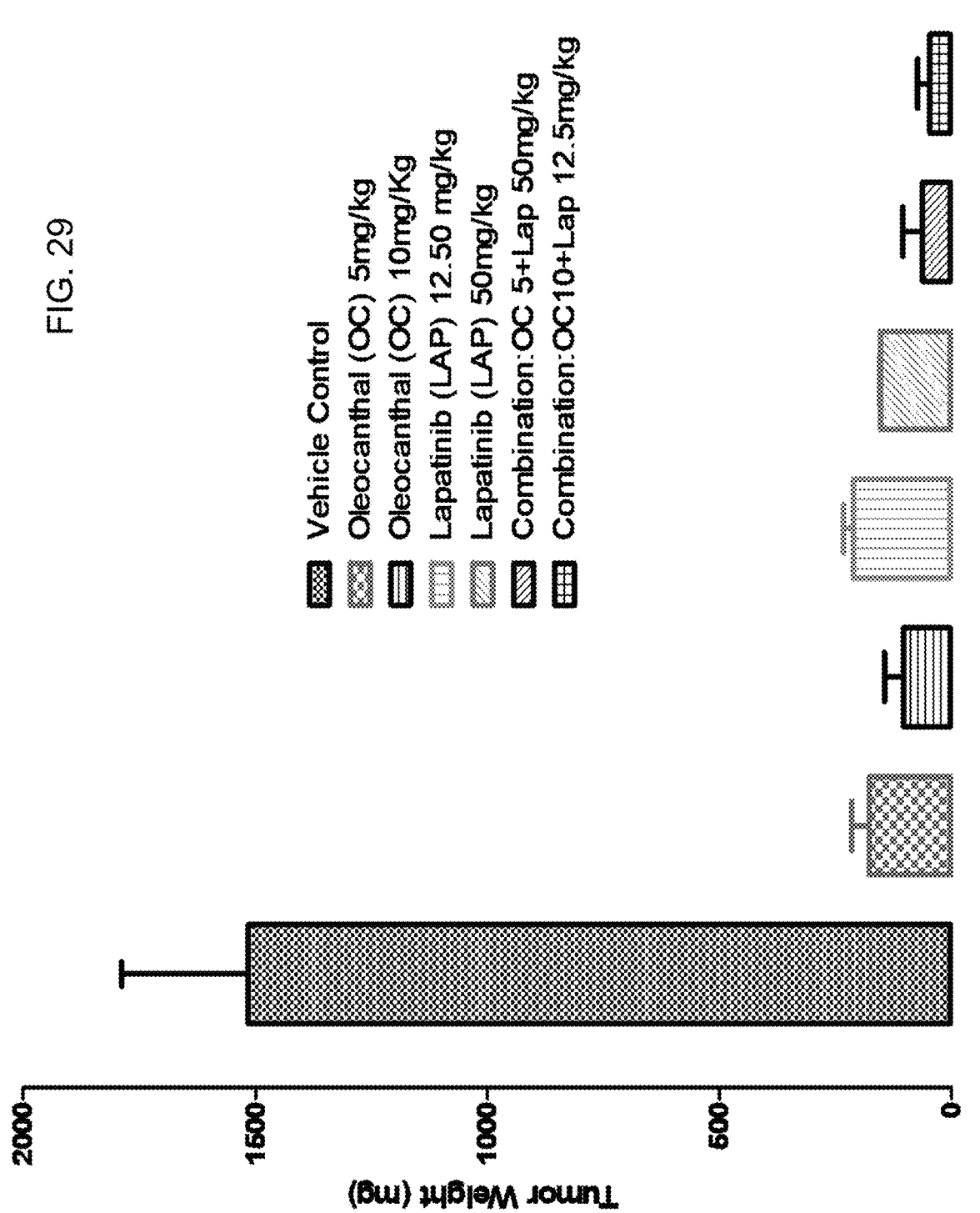

FIG. 36A 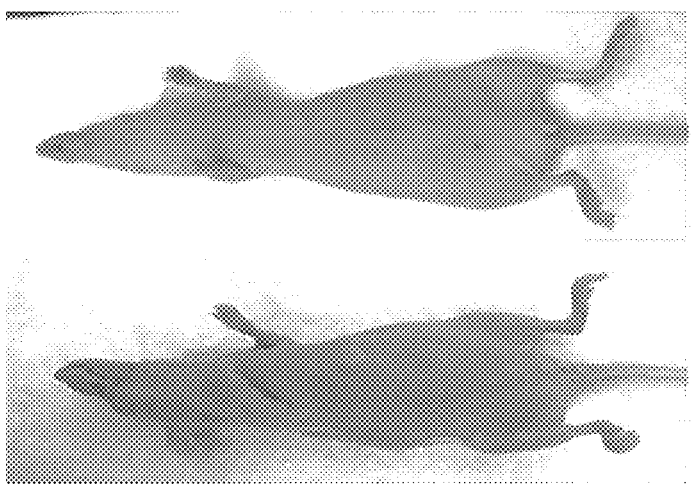 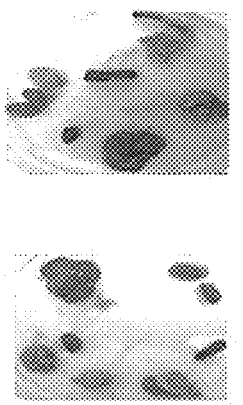
FIG. 36B 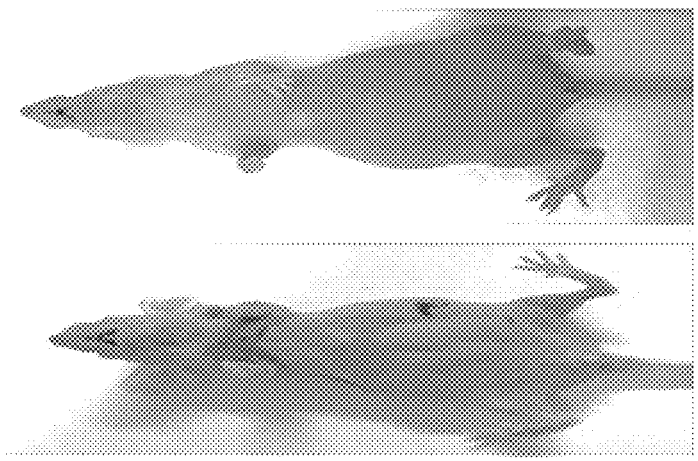 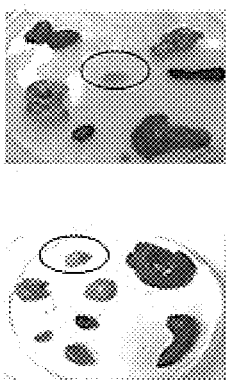
FIG. 36C 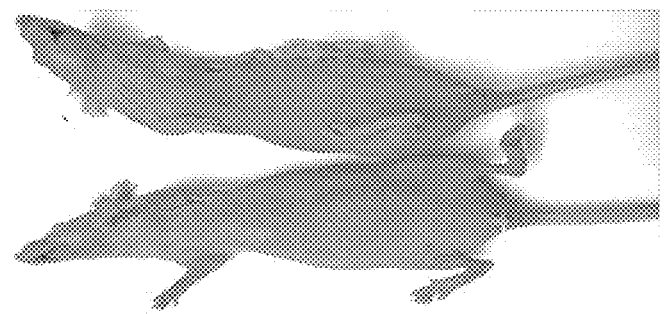 

OLEOCANTHAL ISOLATION AND CANCER TREATMENT

CROSS REFERENCE TO RELATED APPLICATIONS/PRIORITY

The present invention claims priority to U.S. Provisional Patent Application No. 62/365,148 filed Jul. 21, 2016, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

STATEMENT REGARDING FEDERALLY SPONSORED RESEARCH OR DEVELOPMENT

The work described below was supported by Grant No. 1R15CA167475-01, which was awarded by the National Institutes of Health. The Government has certain rights in the invention.

BACKGROUND OF THE INVENTION

About 1.685 million patients are estimated to get cancer in 2016, of which >234,000 will be breast cancer (BC) cases. BC is the most commonly diagnosed cancer in women, which will likely claim the lives of over 41,000 women in 2017. Without the discovery of novel preventive or effective therapy, 846,241 women are expected to die from BC worldwide in 2035. Most BC mortality attributed to metastasis to vital organs, e.g. lung, liver and brain. BC major molecular subtypes classified to luminal A, luminal B, HER2-overexpressing, and basal-like, based on their clinical, histopathological, and microarray criteria. In the US, 73% of tumors are $ER^+$ (expressing ER-$\alpha$) and/or $PR^+$/$HER2^-$, 12% are triple-negative, 10% are $ER^+$ and/or $PR^+$/$HER2^+$, and 5% are $ER^-$/$HER2^+$. Current treatment options include chemotherapy, which pose high degree of morbidity and mortality risks. Surgery followed by chemotherapy resulted in improved survival rates however, nearly ~70% of patients with advanced disease will subsequently suffer tumor recurrence, justifying the need to discover novel recurrence inhibitors. Several women reported to have survived for 5 years will have their BC recur. Despite progress in endocrine chemotherapy, several BC patients have poor recurrence-free and overall survival rates with aggressive and early metastasis behavior regardless of tumor size, grade and number of positive lymph nodes. Chemotherapeutics targeting hormone receptors are initially effective but they quickly develop resistance and can cause serious side effects. Anti-hormonal drugs including ER antagonists like tamoxifen or entities blocking estrogen production like aromatase inhibitors are the main adjuvant and metastatic setting option, but acquired resistance quickly develops, which significantly restricts their therapeutic application. Resistance can be developed via dysregulation of certain growth factors like EGFR, HER2, PI3/AKT, and Ras/Raf/MAPK, which may result in ER ligand-independent activation. Resistance, high cost, and side effects of most $ER^+$ chemotherapeutic classes and lack of recurrence preventive and anti-metastatic drugs motivated the discovery of novel BC recurrence preventives.

Surgical excisions of BC primary tumors and chemotherapy and/or radiotherapy are the most common therapeutic strategies to control solid tumors. Chemotherapeutic agents usually cannot prevent and manage metastatic BC due to the complexity of metastatic cascade. Pharmaceutical industry usually discouraged to invest in antimetastatic drugs because metastasis prevention clinical trials on patients with early-stage cancer with survival and metastases reduction endpoint is not financially feasible and rewarding, since, for example, such trials are extremely long. Yet it remains important to the cancer and pre-cancer patients to discover BC recurrence inhibitors.

In addition to its unsaturated fatty acid content, extra-virgin olive oil (EVOO) contains minor bioactive phenolic compounds such as simple phenols, lignans, and secoiridoids. (-)-Oleocanthal (OC) is a naturally occurring phenolic secoiridoid present in (EVOO), which the inventors have discovered is effective at treating, among other diseases, breast cancer recurrence. Currently, there is a dire need to carry out comprehensive clinical trials on the preventive and curative efficacy of OC in different disease and pre-disease states. Therefore, it is highly demanded to make OC readily available in large quantities in order to enable such clinical research.

The unique structural features of OC rendered its isolation from EVOO very challenging. The available methods to isolate or extract OC from EVOO still have serious drawbacks including the need for sophisticated instruments, massive consumption of organic solvents, and in most of the cases they are expensive, tedious, and time-consuming. Importantly, the majority of OC isolation techniques has poor yield which hinders OC progress through clinical validation pipeline. To bypass different drawbacks associated with OC isolation, recent total synthesis efforts managed to obtain (±)-oleocanthal in eight steps, however, the total synthesis of OC was not stereo- and regioselective, resulting in a racemic mixture in extremely poor overall yield (9%). Previous OC extraction methods also used washing with n-hexanes, with the overall yield being insufficient and the process being time-consuming and having significant OC loss due to cyclic acetal formation. Therefore, there is a dire need to develop a sustainable, time- and cost-effective protocol that can ensure prompt large scale isolation of OC from EVOO and enable its progress into clinical development in therapeutic areas of unmet medical needs.

SUMMARY OF THE INVENTION

Wherefore, it is an object of the present invention to overcome the above mentioned shortcomings and drawbacks associated with the current technology.

The disclosed study established two BC recurrence prevention models: 1) Induction of primary tumors via inoculation of BC cells into the mammary fat pad, creating an orthotopic xenograft growth in female athymic nude mice. Once tumor volume reaches 200 $mm^3$, primary tumor surgically excised and tested compound treatments will be assessed for ability to inhibit tumor recurrence for several weeks. 2) Once orthotopic xenograft model established in nude mice, adjuvant or neoadjuvant chemotherapeutic drug is used for a standard period and stopped. Tested compound treatments will be assessed for ability to reverse chemoresistance and inhibit tumor recurrence.

Therefore, an objective of this study was to develop novel OC isolation techniques useful for practical large-scale use while still time and cost-effective as well as environmental friendly. To mimic the clinical settings, the OC generated emulsion was tested for efficacy and ability to prevent BC recurrence in two models.

Oleocanthal exerted exceptionally potent in vivo efficacy in multiple athymic nude mouse BC xenograft models. Based on the inventors' research, the inventors believe OC sooner or later will become an important dietary supplement to treat and prevent cancers, Alzheimer's and inflammatory disorders. In the current study, multiple novel methods have been developed to isolate OC from EVOO, demonstrating an enhanced performance compared to existing methods which are usually impractical for large-scale OC isolation. A first method involved simple ultra-freezing technique followed by liquid-liquid extraction of EVOO with a single organic solvent. A second method revealed the successful capacity of water to efficiently extract OC from EVOO leading to the discovery of a novel value-added OC-rich self-emulsion. Following water extraction, resin entrapment enabled the quick water and residual fatty acids elimination, recovering OC in high-yield and good purity. Direct water extraction followed by resin entrapment managed to reduce the OC purification process to the minimum; since only a single size exclusion chromatographic step was needed to obtain OC in >95% purity. The proposed water method (or water nano-emulsion method) was applied to multiple EVOO samples from different sources. OC emulsion characterization, stability, and appropriate storage were studied. In vitro and in vivo oral efficacy of OC emulsion revealed significant activity against invasive BC. Oral OC emulsion effectively prevented BC recurrence in two different models: 1—after primary tumor excision and 2—after chemotherapy regimen completion, this suggested the OC emulsion's potential as at least a novel first-in-class dietary supplement BC recurrence preventer, in addition to a preventative and or treatment of other diseases and pre-disease states.

The present invention is directed to methods and apparatuses for isolating OC, for the isolated OC in dried form, and in water and/or other non EVOO liquid, and for treating diseases, such as cancers, with OC alone, and with secondary therapeutics such as kinase inhibitors.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 3 is a schematic representation of the process shown in FIG. 2 where acetonitrile-ultra-freezing for OC extraction from EVOO. The extraction method was applied to several EVOO brands, batches and sources and used thin layer chromatography (TLC), HPLC and q$^1$HNMR analyses for OC quantification and extraction method validation (FIGS. 2-5 and Table 1).

FIG. 8A shows a $^1$H NMR spectrum of the organic residue extracted by $CH_2Cl_2$ from the water extract. OC key characteristic downfield aldehyde signals clearly indicate that OC was solubilized in water layer when shaken with EVOO. FIG. 8B shows an HPLC chromatogram on C-18 RP column using $CH_3C$—$H_2O$ system showing characteristic OC peak with $R_t$=2.8 min. FIG. 8C shows a TLC chromatogram during final OC purification on Sephadex LH-20 showing OC's UV active spot at 254 nm (upper panel) and characteristic brown spot when sprayed with 1% p-anisaldehyde spray reagent (lower panel). FIG. 8D shows a $^1$H NMR spectrum of >95% pure OC after single step Sephadex LH-20 size exclusion column chromatography purification. FIG. 8E shows a pure OC peak on HPLC C-18 RP column after Sephadex LH-20 purification. FIG. 8F shows the HPLC standard calibration curve used to quantify OC contents in different EVOO batches and fractions. FIG. 8G shows a $^1$H NMR spectra of various OC pure samples used to make the standard calibration curve using quantitative $^1$H NMR analysis, which is shown in FIG. 8H.

FIG. 9 is a table of validation and reproducibility of water nano-emulsion extraction method using various EVOO batches, labeled Samples 1-8. WE: Water extraction; Ex: Extraction; EVOO: Extra-virgin olive oil; NP: Did not proceeded due to low oil amount available; NA: Not available; NN: Not needed because there was no OC content. The quantity is considered based on (1:3) EVOO: Water ratio. It was observed that EVOO batches with high OC concentration preferably used additional 2-3 extraction cycles to reach 95% of recovery. Pure quantity considered after purification using Sephadex LH-20 column chromatography.

FIG. 11A shows a $^1$H NMR spectrum of SP-70 Acetone-eluted fraction containing OC. FIG. 11B shows a $^1$H NMR spectrum of SP-70 water-eluted fraction extracted with CH$_2$Cl$_2$ and the residue was dissolved in CDCl$_3$ and used for analysis. Water-eluted fraction contains only unsaturated and hydroxy-fatty acids and showed no OC content. FIG. 11C shows a $^1$H NMR spectrum of XAD-7 acetone-eluted fraction containing OC. FIG. 11D shows a $^1$H NMR spectrum of XAD-7 CH$_2$Cl$_2$ extract of the water-eluted fraction. Water-eluted fraction contains only unsaturated and hydroxy-fatty acids and showed no OC content. FIG. 11E shows a $^1$H NMR spectrum of the Diaion HP-20 acetone-eluted fraction containing OC. FIG. 11F shows a $^1$H NMR spectrum of the Diaion HP-20 CH$_2$Cl$_2$ extract of the water-eluted fraction. Water-eluted fraction contains only unsaturated and hydroxy-fatty acids without any OC content.

FIGS. 20, 21A and 21B, 22 and 23 show (-)-Oleocanthal nano-emulsion oral treatment suppresses human TNBC MDA-MB-231 cells growth in orthotopic mouse xenograft model. MDA-MB-231/GFP human breast cancer cells were cultured and resuspended in serum-free DMEM medium (20 µl). After anesthesia, cell suspensions (1×10$^6$ cells/20 µl) were inoculated subcutaneously into the second mammary gland fat pad just beneath the nipple of each athymic nude mouse to generate orthotopic breast tumors. At 48 h post-inoculation, the mice were randomly divided into two groups: i) the vehicle-treated control group (n=5), ii) the (-)-Oleocanthal emulsion treated group (n=5). Treatment started 07 days pre inoculation with oral administration using oral gavage vehicle control or 10 mg/kg (-)-Oleocanthal emulsion everyday. FIG. 20 is a line chart showing tumor size was evaluated periodically during treatment at indicated days postinoculation. Tumor volume (V) was calculated by V=L/2×W$^2$, where L was the length and W was the width of tumors. Points, mean of tumor volume in mm$^3$ of several tumors (n=5) during the course of the treatment period; FIGS. 21A and 21B show two mice harboring human breast cancer and their associated breast tumors. FIG. 21A is a photograph of a vehicle treated control mouse. FIG. 21B is a photograph of a mouse with suppression of tumor growth with (-)-Oleocanthal emulsion treatment (10 mg/kg/day). FIG. 22 is a line chart showing no significant change in body weight was observed among treated animals, indicating the safety of (-)-Oleocanthal emulsion treatment. FIG. 23 is a bar graph where the vertical bars indicate mean tumor weight at the end of the experiment.

FIG. 24A is five photographs of mice used in previous oral efficacy experiment that were subjected to primary tumor excision surgery on the 35$^{th}$ day of treatment. FIG. 24B is five photographs of mice orally treated with 10 mg/kg OC nano-emulsion for 30 more days, then sacrificed and five photographs of their tumors (n=5), along with two photographs of mice from vehicle-treated control group and two photographs of their tumors. As shown, OC treatment inhibited TNBC recurrence in 4 out of 5 mice.

FIG. 25 is a line chart showing OC nano-emulsion additional 30-days oral treatment inhibited TNBC recurrence in 4 out of 5 mice with >95 tumor recurrence inhibition after primary tumor excision on the 35$^{th}$ day of initial treatment. FIG. 26 is a bar graph comparing mean tumor weight of the treated and control mice. FIG. 27 is line chart showing oral daily OC nano-emulsion treatment 10 mg/kg for 65-days did not affect mice body weight.

FIGS. 28A-28C show OC in vivo activity against the HER2$^+$-ER$^+$ breast malignancy. 5×10$^6$ cells/20 µL BT-474 human BC cells were sc inoculated into second mammary gland fat pad of athymic nude (Foxn1$^{nu}$/Foxn$^1$). Mice randomly divided to Vehicle-treated control group, shown in FIG. 28A, and OC-treated groups (n=6, each) at 5 mg, shown in FIG. 28B, and 10 mg/kg, shown in FIG. 28C, ip treatments (3×/week, 60-days). Top panels show photographs of representative intact animal for each group. Bottom panels show photographs of excised primary tumor at experiment end.

FIGS. 29-32 show OC in vivo activity against the HER2$^+$-ER$^+$ breast malignancy. OC 5 mg and 10 mg/kg, 3×/week for 60 days significantly and dose-dependently inhibited, as it compared with vehicle and lapatinib controls, the BT-474 tumor weight, as shown in the bar graph of FIG. 29, and tumor volume as shown in line charts of FIG. 30 and FIG. 31, with FIG. 31 being the same data as FIG. 30, without the control line. In FIG. 31, at the 60 day mark, the top line is lapatinib at 12.5 mg/kg, the second highest line is OC at 5 mg/kg, the third highest line is lapatinib at 50 mg/kg, the fourth highest line is OC at 10 mg/kg, the fifth highest line is a combination of OC 10 mg/kg and lapatinib 12.5 mg/kg, and the lowest line is a combination of OC 5 mg/kg and lapatinib 50 mg/kg. FIG. 32 is a line chart showing that OC treatments did not significantly affect mice average body weight over the 2-month experiment period.

FIG. 33 is a bar graph showing OC 10 mg/kg, 3×/week for additional 54 days significantly inhibited recurrence BT-474 tumor weight as it compared with vehicle and lapatinib 50 mg/kg controls. FIG. 34 is a line chart that shows the same treatment significantly inhibited recurrence tumor volume as it compared with vehicle and lapatinib 50 mg/kg controls. FIG. 35 is a line chart showing OC treatments did not significantly affect mice average body weight over the additional 54 days experiment period.

FIGS. 36A-36C show that OC inhibits the HER2$^+$-ER$^+$ breast malignancy recurrence in vivo after 50 mg/kg lapatinib regimen. FIG. 36A is a photograph of representative animals of vehicle control group and two photographs showing circled tumor developed over the additional 54 days period. FIG. 36B is two photographs of representative animals that completed 60 days oral lapatinib 50 mg/kg group and two photographs of developed circled tumors after additional 54 days. FIG. 36C is two photographs of representative animals of 10 mg OC 1p, 3×/week group, and two photographs showing no tumor developed over the additional 54 days regimen.

DETAILED DESCRIPTION OF THE PREFERRED EMBODIMENTS

Figure 1:
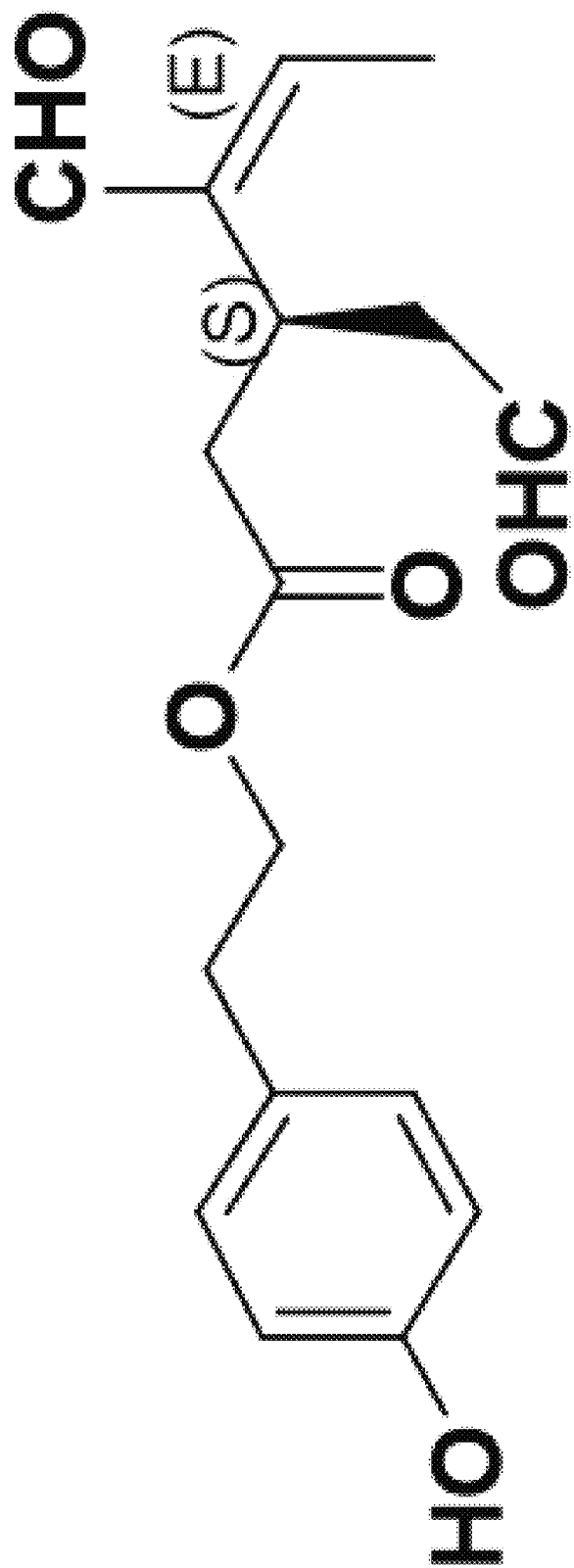
FIG. 1 is a schematic representation of the chemical structure of (-)-oleocanthal (OC).

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-36C, a brief description concerning the various components of the present invention will now be briefly discussed.

OC Improved Extraction Methods

Acetonitrile-Ultra-Freezing (-)-Oleocanthal Extraction Method from EVOO

EVOO's major content is represented by glycerol, triglycerides, and fatty acids (99%), while the remaining 1% is composed of several minor bioactive phenolic compounds including OC. OC's chemical structure is shown in FIG. 1. Therefore, isolating such minor phenolics in pure form and in acceptable yield is challenging. In previous attempts, OC was isolated from EVOO via the tedious and time-consuming liquid-liquid extraction procedure using very large amounts of methanol and n-hexanes in subsequent extractions. The dried methanolic fraction was then subjected to repeated medium pressure liquid chromatography on lipophilic Sephadex LH20 followed by high performance liquid chromatography (HPLC) analysis to isolate OC in a pure form but in a poor yield. The inventors realized that there were at least three major limitations regarding this procedure; firstly, the large consumption of organic solvents, secondly, the poor yield due to the loss of OC during acetalization by methanol, and finally the lack of time and cost-effectiveness.

Figure 2:
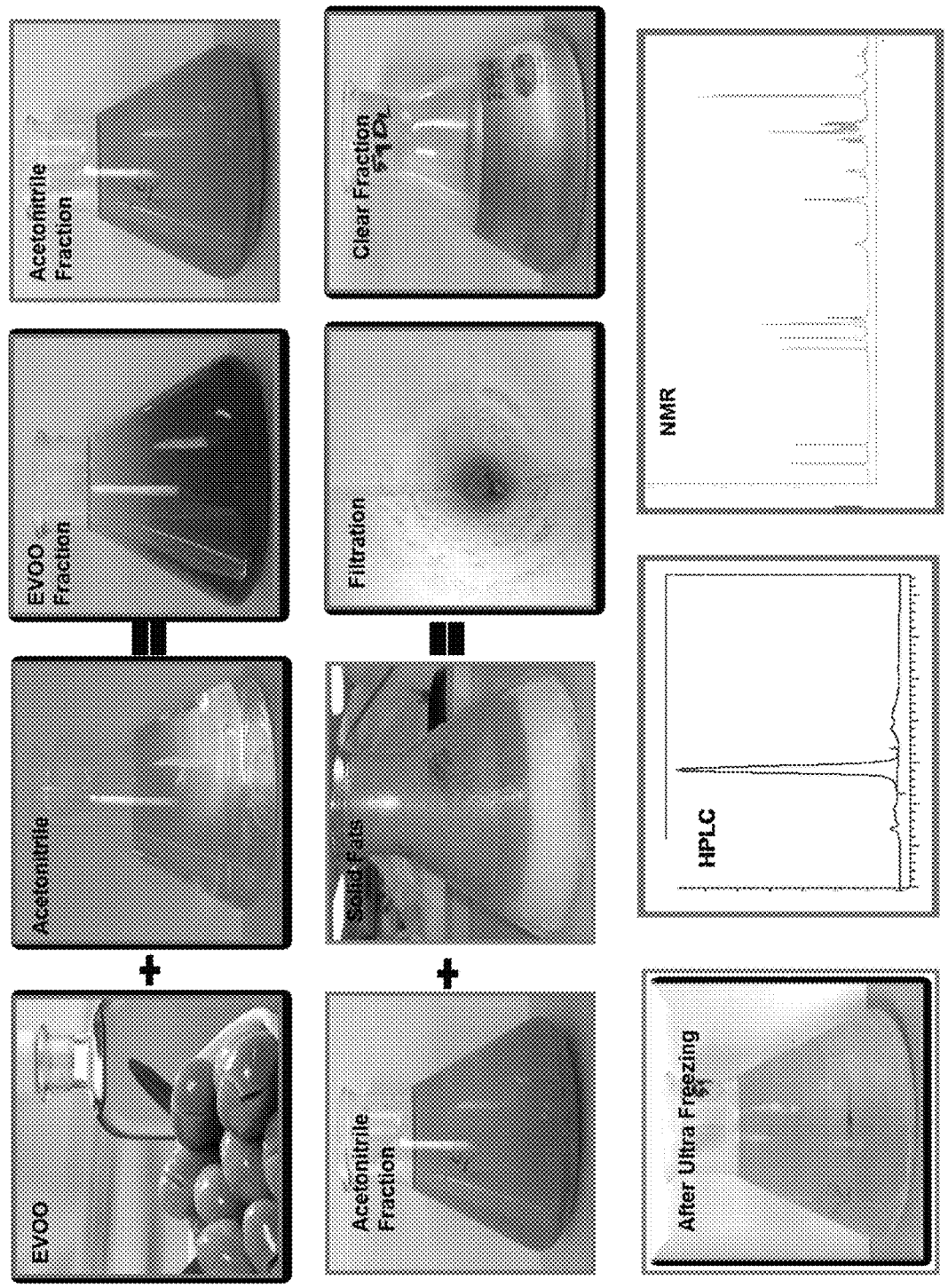
FIG. 2 is a photographic flow chart of an acetonitrile method of (-)-oleocanthal isolation. EVOO is subjected to simple extractions with acetonitrile followed by immediate repeated ultra-freezing and finally freeze drying to get gram-scale amount of OC.
Figure 4:
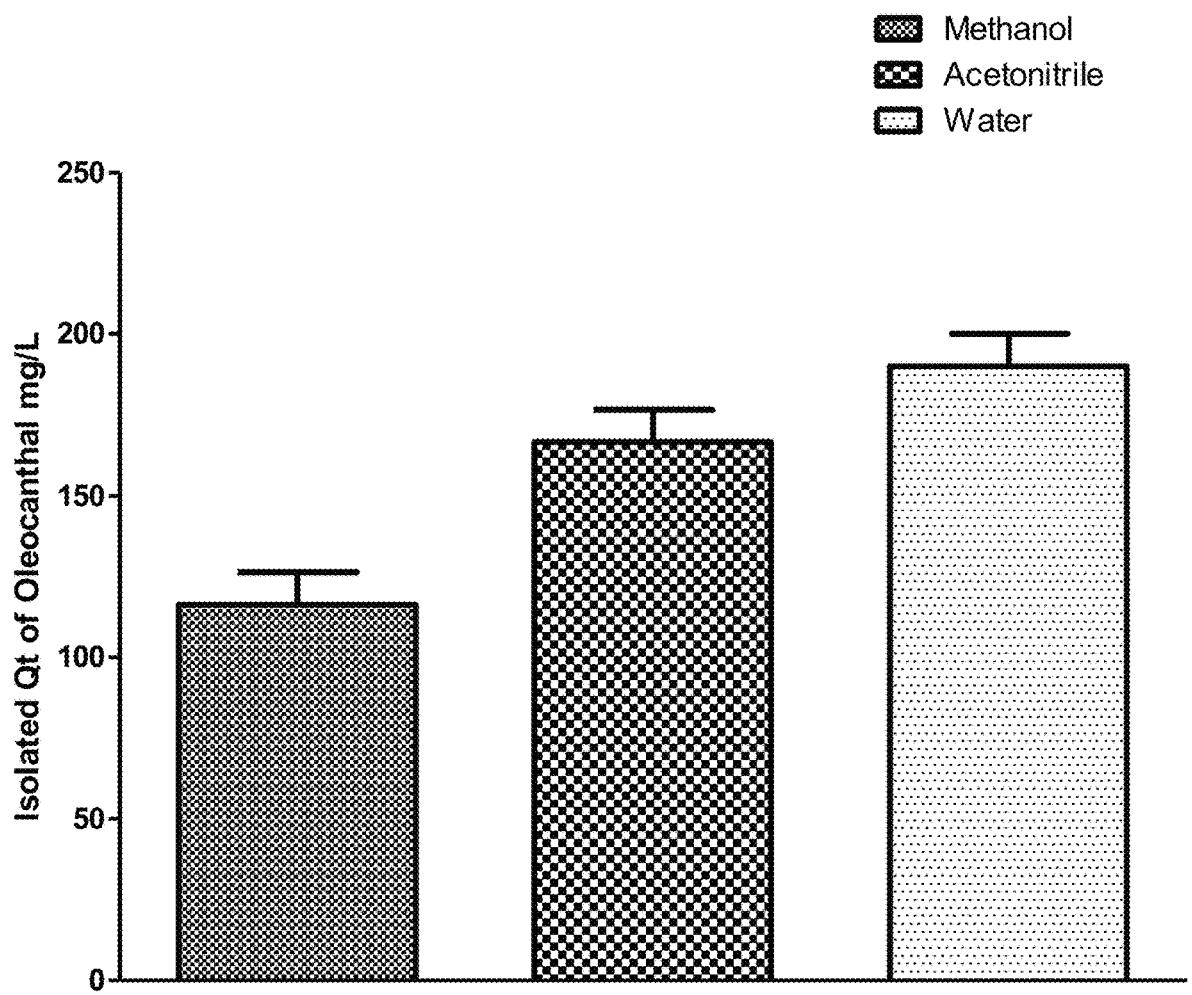
FIG. 4 is a graph showing a comparison of the OC yield using the three isolation methods methanol, acetonitrile-ultra-freezing, and water nano-emulsion. OC yield significantly improved using the acetonitrile-ultra-freezing and water nano-emulsion method.

In an attempt to improve the previous method, the inventors successfully attempted two effective modifications. Firstly, the evaporation of methanol and reconstitution of the extract in chloroform reversibly afford again the aldehydic form of OC. There is no exact recovery statistics to confirm whether this reaction is quantitative and ultimately some OC is lost in this reaction regardless of the reaction condition. In order to eliminate the possibility of OC loss due to the expected acetal or hemiacetal formation, the inventors replaced methanol with acetonitrile during the extraction procedure. The inventors are aware that acetonitrile does not react with any analytes when used as a solvent for extraction of EVOO. To ensure exhaustive extraction, the EVOO sample was extracted for three consecutive times with acetonitrile to get the majority of OC content present in EVOO out. See FIGS. 2 and 3. Secondly, an ultra-freezing protocol was applied to the acetonitrile fraction via storing at −80° C. for one hour, for three consecutive cycles (FIG. 3). The inventors hypothesized that the major fatty fraction of the acetonitrile extract would solidify and form a precipitate under ultra-freezing conditions, while minor phenolics will remain in a liquid form. As expected, enormous amount of the fatty acid fraction was solidified and fully precipitated in the bottom of the container (FIG. 2). Through a simple filtration procedure, the solidified fatty fraction is retained on the filter paper, eliminated and a clear oily solution containing OC was collected after each ultra-freezing cycle (FIGS. 2 and 3). $^1$H NMR and HPLC analysis of the dried acetonitrile extract clearly showed a significant reduction in the amount of fatty fraction compared to the initial dried extract without ultra-freezing (FIG. 2). Since more than 50% of the fatty acid fraction was removed during the ultra-freezing process, a single final purification step using Sephadex LH20 column chromatography with isocratic CH2CL2 elution was sufficient to timely and cost-effectively obtain pure OC (>99% purity). It is worth noting that the OC's yield has been significantly improved upon applying the acetonitrile-ultra-freezing extraction protocol, which confirmed its superior efficiency over the initial methanol-room temperature extraction method (FIG. 4).

Figure 5:
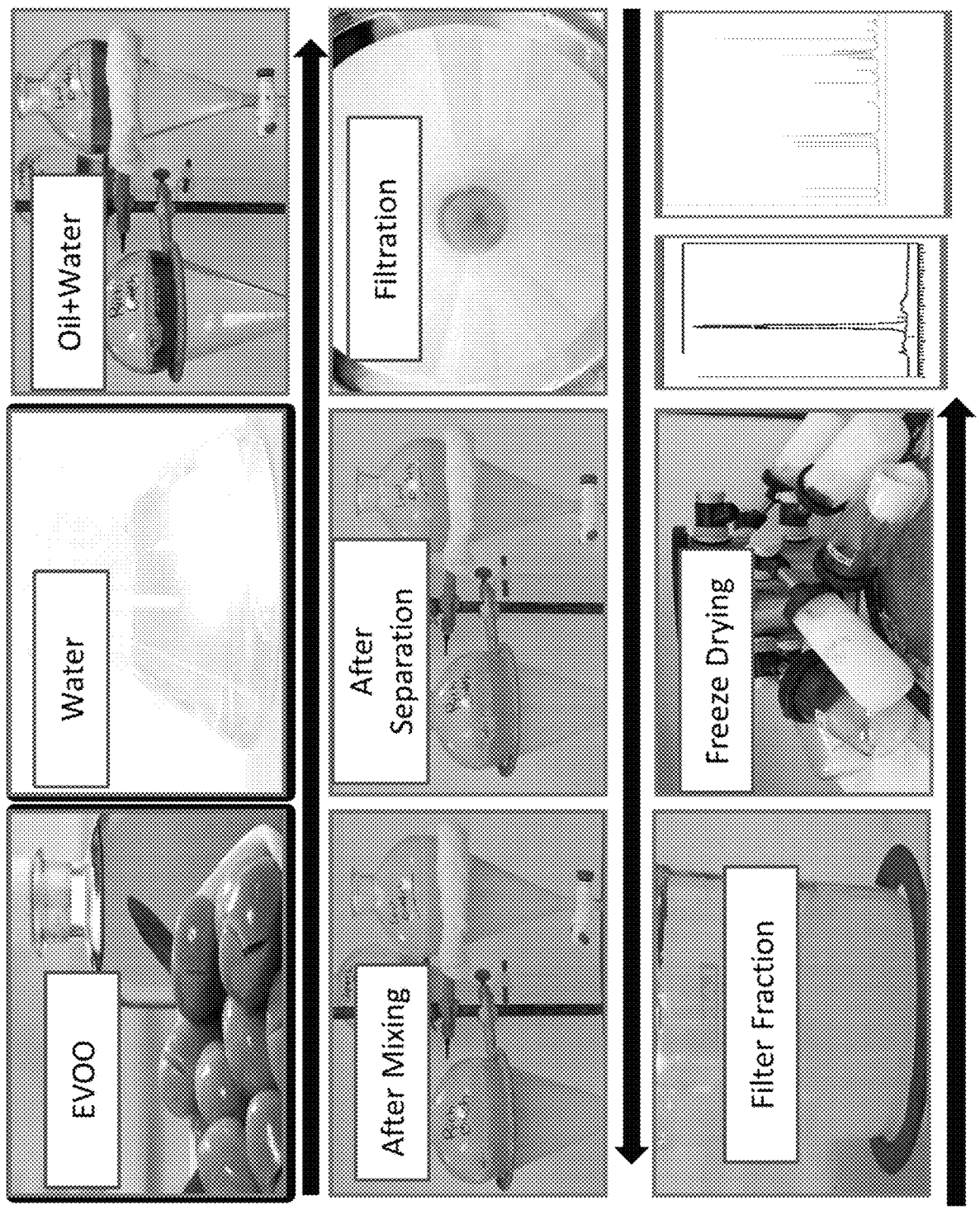
FIG. 5 is a photographic flow chart of a water nano-emulsion method of OC isolation.
Figure 6:
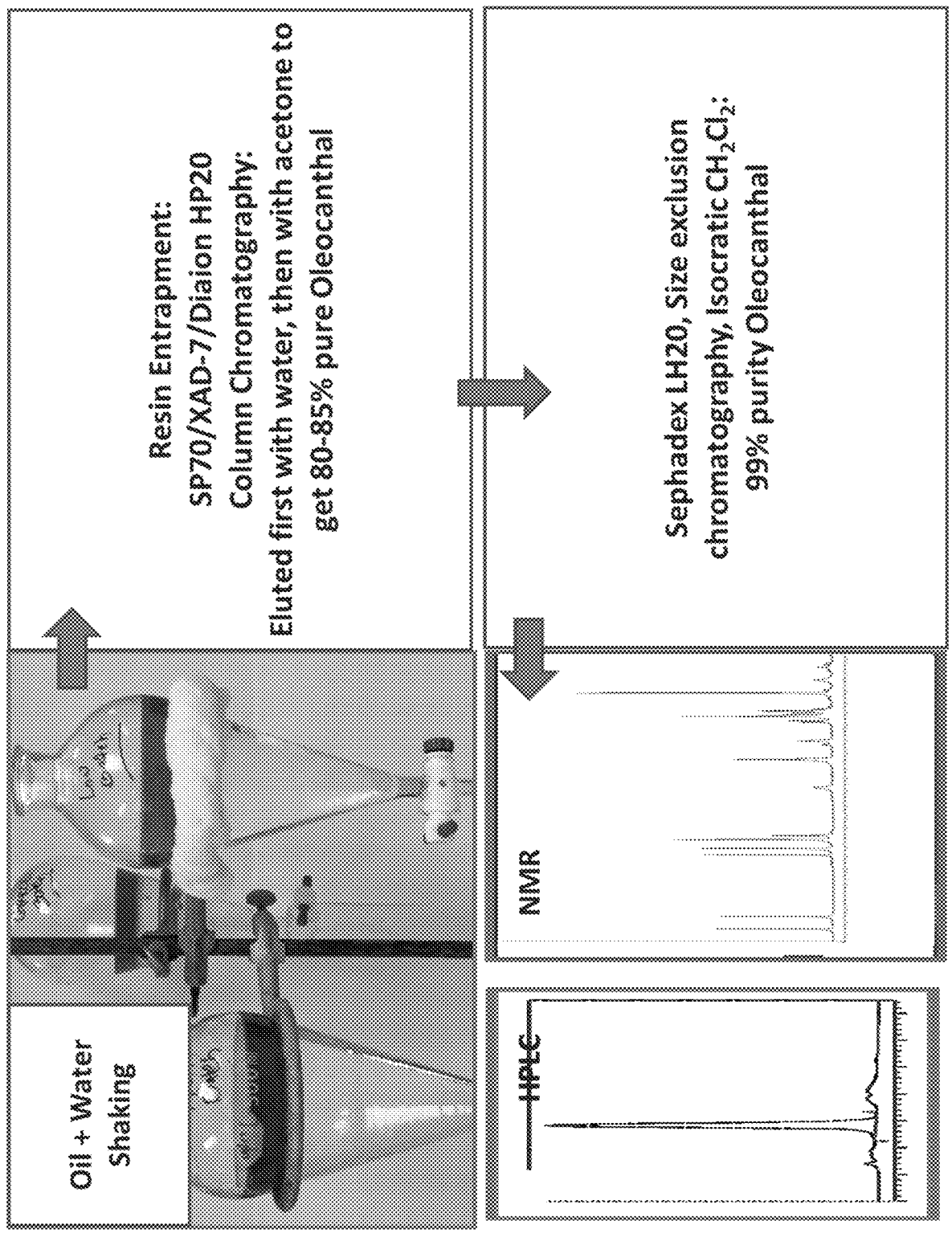
FIG. 6 is a partial photographic flow chart of a modified water nano-emulsion method of OC isolation using resin entrapment.
Figure 7:
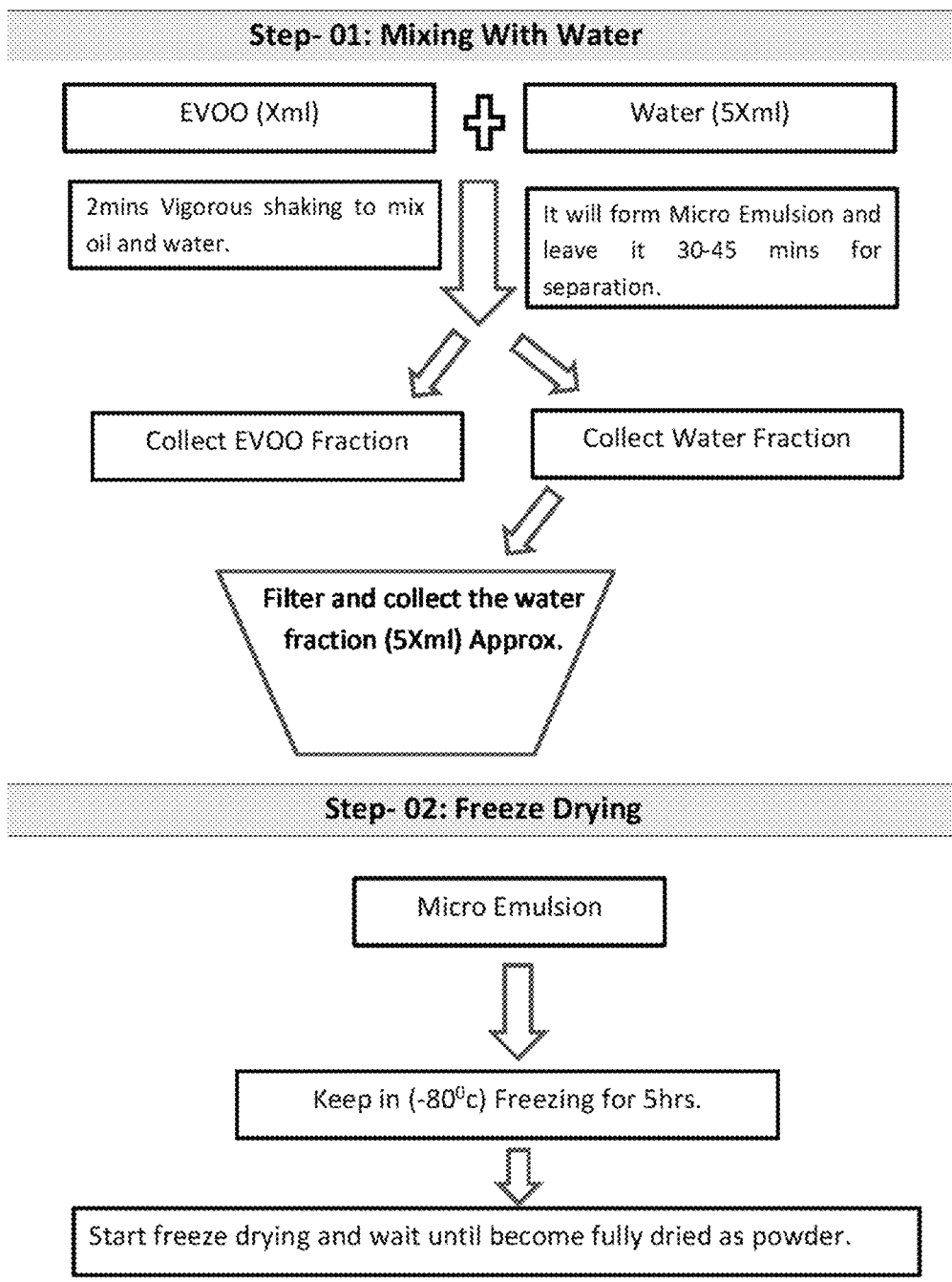
FIG. 7 is a schematic representation of the process shown in FIG. 5. The water nano-emulsion extraction method was applied to several EVOO brands and sources and used thin layer chromatography (TLC), HPLC and q$^1$HNMR analyses (FIGS. 2-5) to validate the extraction method. The results of oleocanthal extractions are presented in the table shown in FIG. 9.

Novel Oleocanthal Self-Emulsifying Extraction Method from EVOO and Proposed Added-Value "Oleocanthal Water" Product Though the acetonitrile-ultra-freezing method is efficient for extracting OC from EVOO, it still has some drawbacks. Firstly, the capacity of space in the −80 0° C. facility can be limited and may not be suitable for large-scale isolation of OC. Secondly, the acetonitrile-ultra-freezing method suffers from a large amount of organic solvent consumption which has two serious drawbacks; one, organic solvents may not be environmental friendly, and two, the exhausted EVOO following organic solvent extraction likely cannot be reused. The inventors were aware that OC has the ability to dissolve in polar as well as non-polar solvents. Thus, OC seems to possess an amphiphilic property. The inventors are aware that OC undergoes a spontaneous interaction with water leading to the formation of reversible mixtures of hemiacetals or acetals, by the addition of D2O molecule to one of OC's aldehydes, characterized using 1D and 2D NMR spectra, from which OC can be regained back after D20 removal. Consistently, the inventors noticed the disappearance of one characteristic aldehydic proton peaks of OC when the $^1$HNMR spectrum was run in deuterated water (δ9.41). Meanwhile, the regular $^1$HNMR spectrum of OC in CDCl$_3$ shows both distinctive aldehydic peaks (δ9.20 and 9.41), when the same sample is dried and used for analysis. Based on these data, the inventors hypothesized that OC might reversibly interact with water in a similar manner to reversibly form its amphilic more polar acetal form. Since water is readily available, cost effective, as well as environment friendly solvent and taking into consideration its proposed spontaneous and reversible interaction with OC, the inventors hypothesized that water can be the appropriate solvent for large scale extraction of OC from EVOO. In other words, the inventors decided to use of the water-OC reversible interaction to selectively isolate OC from its crude fatty acid containing parent source EVOO. Accordingly, EVOO was extracted three consecutive times with water via a simple liquid-liquid extraction protocol and the water fractions were collected (FIGS. 5 and 7). As expected, once EVOO was mixed with water it formed an emulsion. Thus, the process can be considered as a self-emulsifying extraction method (FIG. 5). A quantitative study was then carried out to determine the amount of OC in the resultant emulsion as well as in EVOO before and after water extraction using HPLC (FIGS. 8A-8H and 9). As expected by the inventors, OC was mostly shifted to the water layer, with negligible amount of fatty acids, dropping out the majority of fats in the oil layer FIGS. 8A-8H and 9. After three water extraction cycles, 5-10% of OC content remained in EVOO, compared to the fresh EVOO batch, and nearly 90-95% of OC has been shifted towards water layer as determined by HPLC (FIG. 9). Later, the residual amount of OC left in EVOO can be carried over by additional water extraction cycles. Furthermore, the resultant emulsion was subjected to freeze drying for 24-48 h to identify its ingredients using TLC and q-$^1$HNMR analyses (FIGS. 5, 7, and 8A-8H). The water extract afforded ~80-85% pure oleocanthal with ~15% monounsaturated fatty acids, containing mainly oleic acid, and the rest is minor EVOO phenolics, as evidenced by TLC, q-1HNMR and confirmed by HPLC analyses (FIG. 8A-8H). In addition, the percentage recovery of OC using the water self-emulsifying method was calculated and found to be around 90-100% after the fifth extraction round (FIG. 9). These results strongly confirm the efficiency of the water extraction method and supporting the proposed hypothesis regarding selective OC extraction from EVOO when water is used as extraction solvent. Since water was used as an extraction solvent, this novel OC self-emulsifying extraction method has a significant advantage over all previously reported methods, where organic solvents have been used. The resulting EVOO after water extraction can be reused back in food industry; meanwhile, it will be much less bitter and pungent in taste due to the removal of OC, the main ingredient responsible for the pungent taste of EVOO. In other words, the disclosed method will not only extract OC from EVOO in an advantageous recovery percentage, but it allow for the OC-removed and less pungent EVOO to be further used in the food industry.

Resin Entrapment as a Suitable Alternative for Freeze Drying

Figure 10:
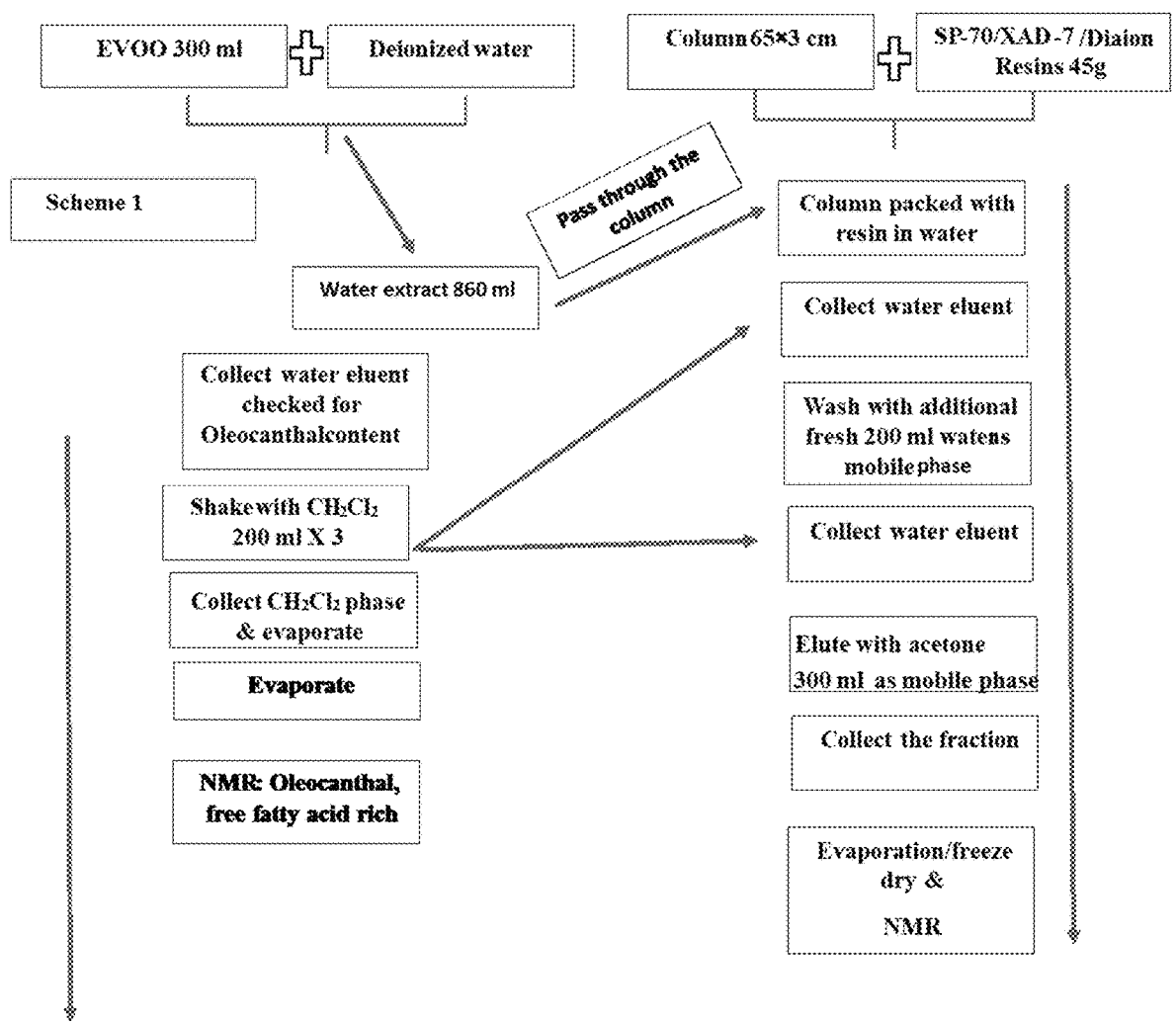
FIG. 10 is a schematic representation of the process shown in FIG. 6, using resins (SP-70, XAD-7, and Diaion HP-20) to eliminate water and purify OC.
Figure 11A:
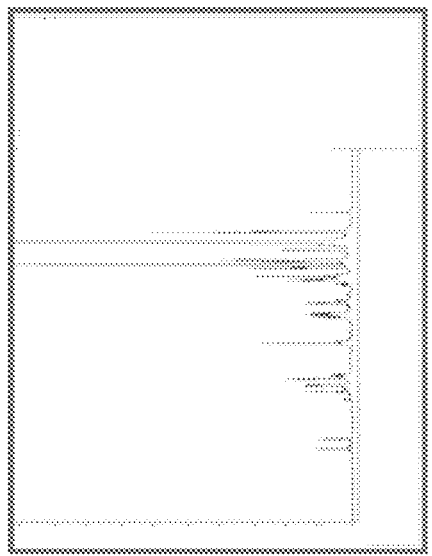
FIGS. 11A-11F are $^1$H NMR-guided monitoring OC entrapments on various resins using JEOL ECS-400 in CDCl$_3$.
Figure 11C:
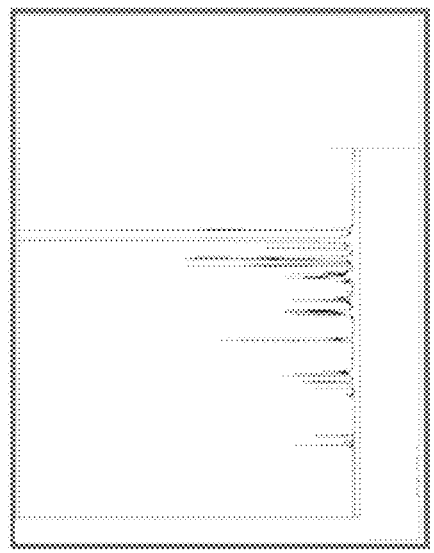
Figure 11E:
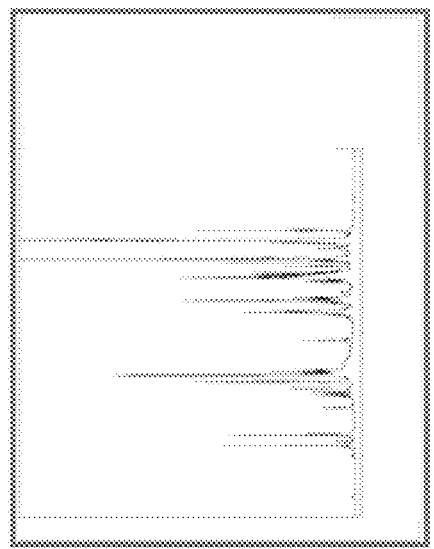
Figure 11B:
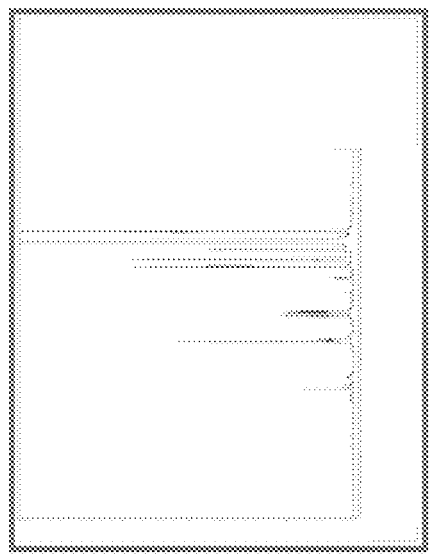
Figure 11D:
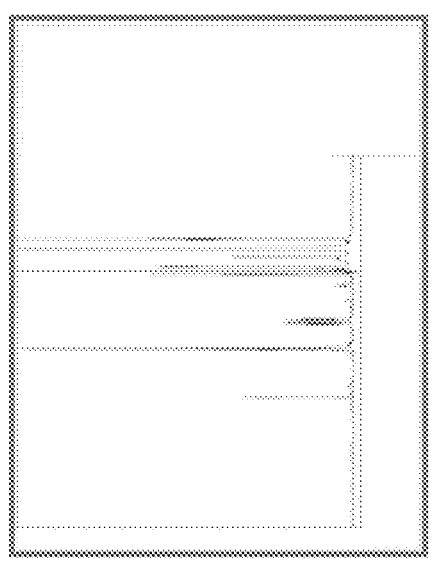
Figure 11F:
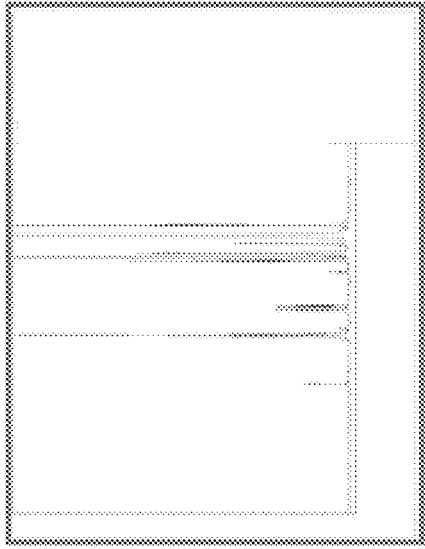
Figures 12A, 12B, 12C:
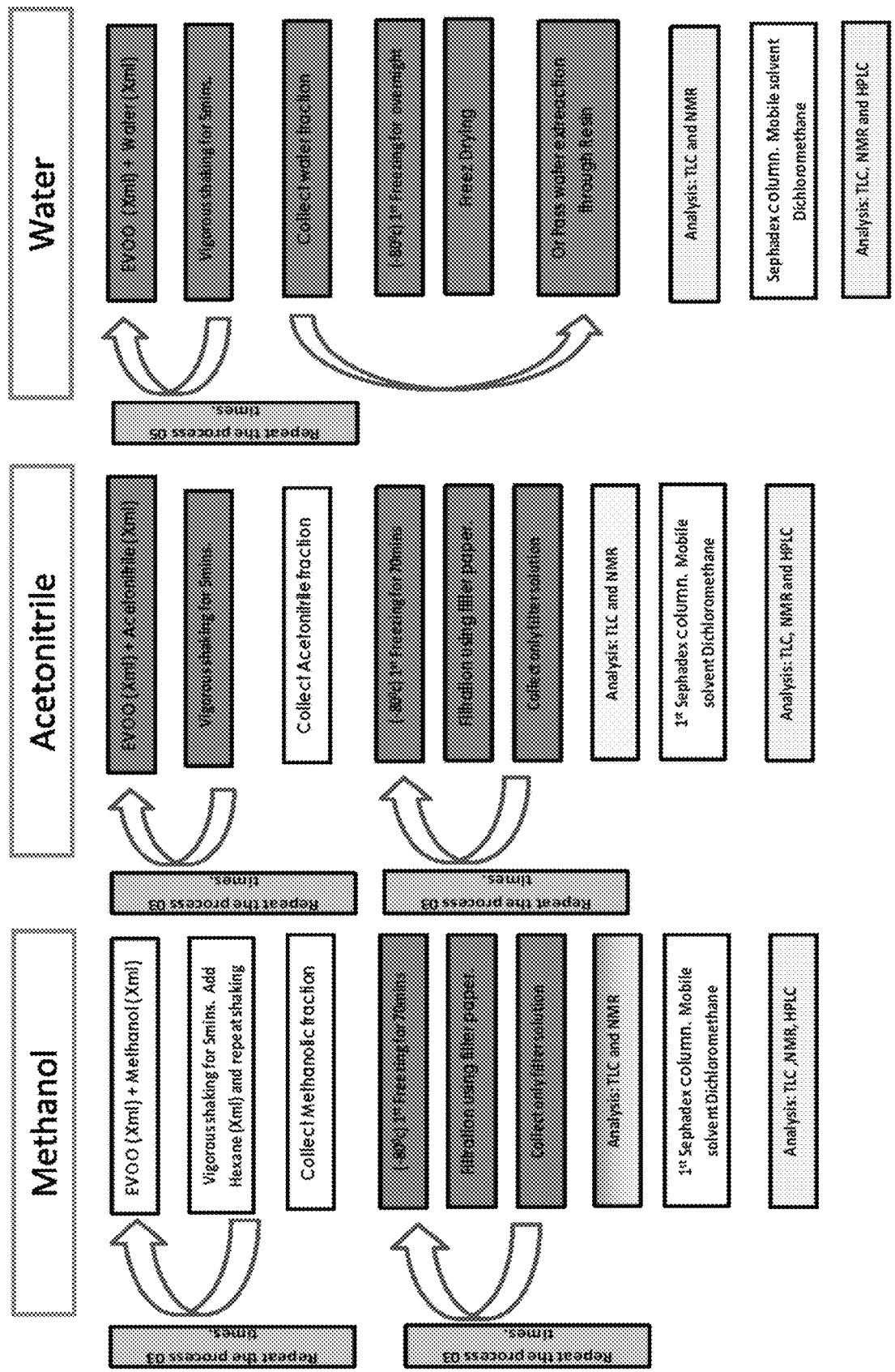
FIGS. 12A-12C are schematic flow charts representing methods of OC isolation with FIG. 12A showing methanol extraction, FIG. 12B showing acetonitrile-ultra-freezing extraction, and FIG. 12C showing water nano-emulsion extraction.

The OC self-emulsifying extraction method described above preferably uses multiple hours freeze drying to evaporate water and get OC-rich extract (FIG. 7). However this process is time-consuming and may slightly affect OC yield over extended freeze drying hours. To overcome these potential drawbacks and make OC water extraction method more practical on large-scale, wet pack resin adsorbent beads were used as freeze drying alternative to remove water and improve purity (FIG. 10). Three different types of resin have were utilized in experiments, including: SP-70, Amberlite XAD-7, and Diaion HP-20 resins. Simply, the OC-containing emulsion was passed over a column packed with each resin type in water and the eluent was collected after using water as a mobile phase (FIG. 10). The water eluent was extracted with CH$_2$Cl$_2$ to test any escaped OC content, dried, and subjected to $^1$HNMR analysis (FIGS. 10 and 11A-11F). The three types of resin used herein managed to successfully fully entrap OC as evidenced by the lack of characteristic OC $^1$HNMR signals in their corresponding water eluents (FIGS. 11A-11F), but other reins may also be used. Interestingly, the water fractions contained only unsaturated and hydroxy-fatty acids as shown in their corresponding $^1$HNMR spectra, which may also imply the efficiency of the resin beads in conferring further purification of the OC fraction (FIG. 3D and FIGS. 11A-11F). The resin-packed columns were finally washed with acetone, to allow the elution of the entrapped OC, and the acetone fractions were collected, dried, and analyzed using 1HNMR (FIGS. 10 and 11A-11F). Acetone was selected for OC elution because it is a non-halogenated, biodegradable, water miscible, environment friendly, and inert will not acetalize OC. As expected, the $^1$HNMR spectra of the acetone fractions demonstrated full recovery of OC (FIGS. 11A-11F), suggesting the efficiency of the three resin types to selectively entrap OC and eliminate water and residual fatty acid impurities and therefore presenting an alternative to the freeze drying step. The acetone fractions showed significant OC purity improvement (80-90%), with nearly complete elimination of fatty acid impurities, with >90% OC recovery based on $^1$HNMR and HPLC analysis of the acetone and water eluates (FIGS. 9 and 11A-11F). SP-70 was the most efficient resin to entrap OC, followed by Amberlite XAD-7, and finally the Diaion HP-20 resin. Overall, these results suggest that any or all of the three resins, for example, can be successfully used to quickly eliminate water and fatty acids and recover OC in a high yield. It is worth noting that the water extraction method along with resin entrapment managed to reduce the OC purification process to dramatically, as, for example, in one embodiment only a single Sephadex LH-20 size exclusion chromatographic column was used, with isocratic $CH_2Cl_2$ elution, to obtain OC in >99% purity (FIG. 12C). In addition, the proposed water extraction method for OC from EVOO showed an enhanced performance, in terms of OC yield and purity, compared with methods which involve the use of organic solvents such as methanol and acetonitrile (FIG. 3). The disclosed OC water isolation method (also called the water extraction protocol, the water nano-emulsion method, the nano-emulsion method, or the self-emulsion method) offers cost and time-effective elimination of water and fatty acids with possible practical future use for the OC free EVOO and for OC large-scale production.

Self-Emulsified OC Characterization

Figure 13:
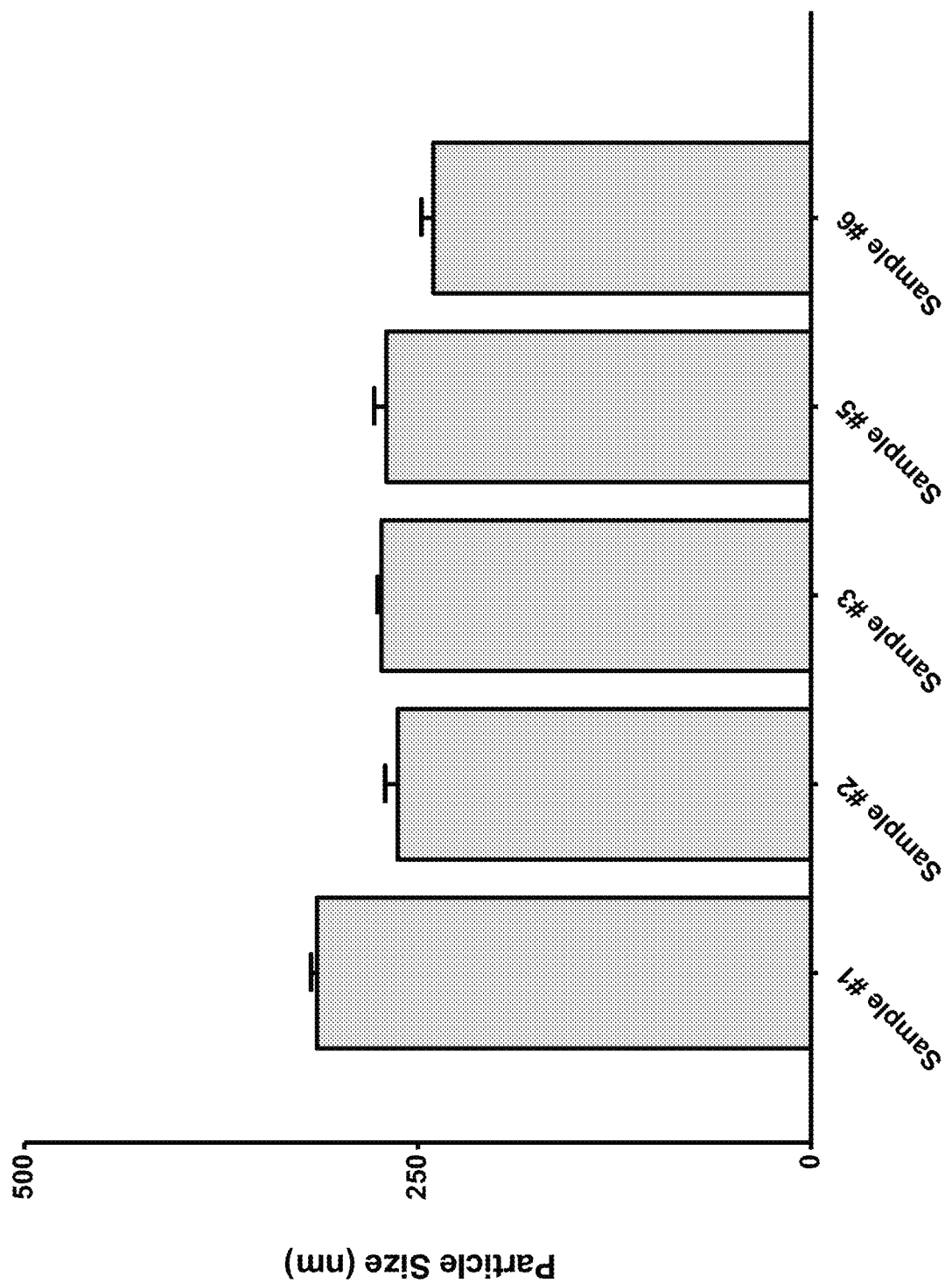
FIG. 13 is a bar graph of particle size measurement of OC nano-emulsion of Samples 1-6 in FIG. 9.
Figure 14:
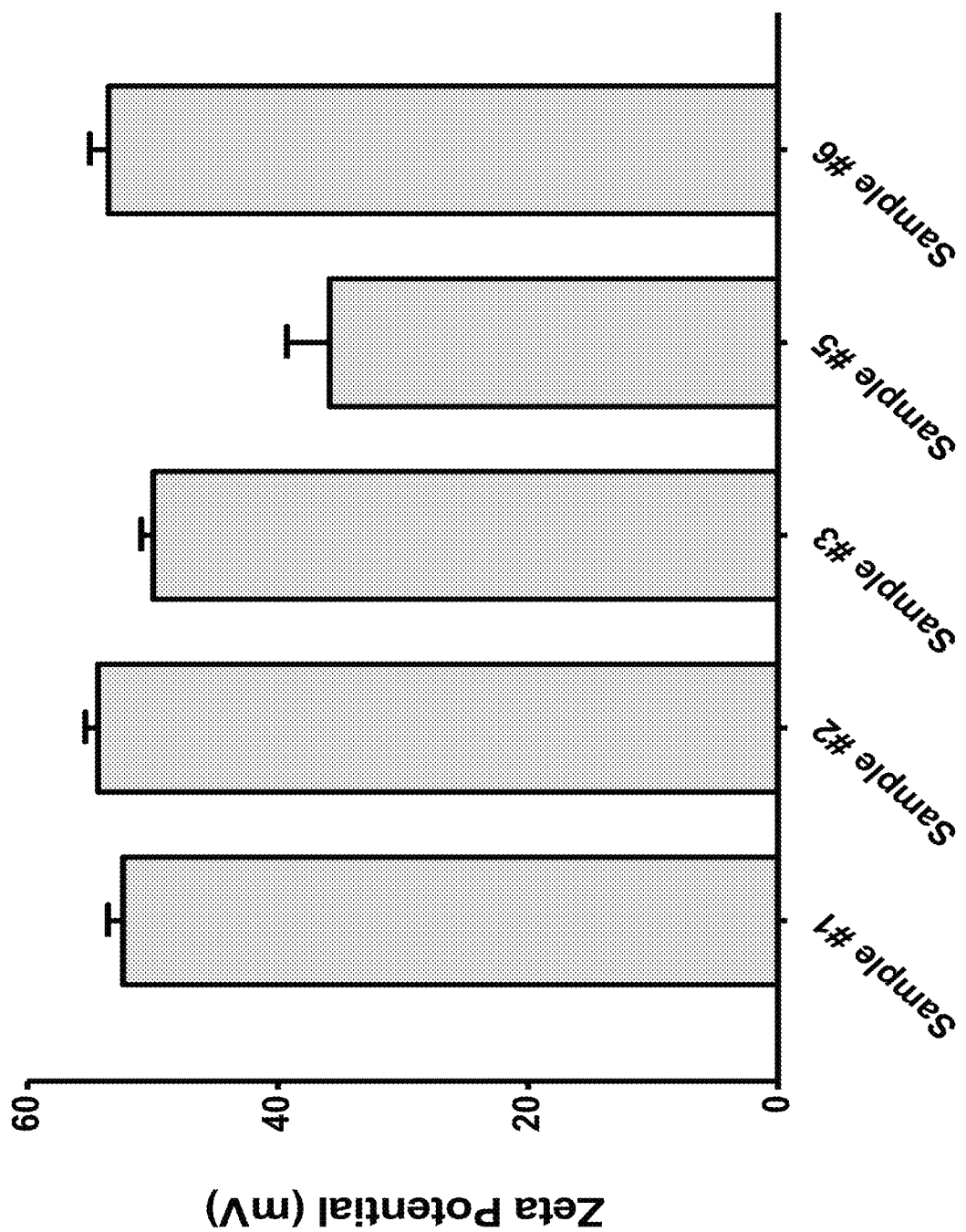
FIG. 14 is a bar graph of the polydispersity index of the six samples of OC nano-emulsion in FIG. 13.
Figure 15:
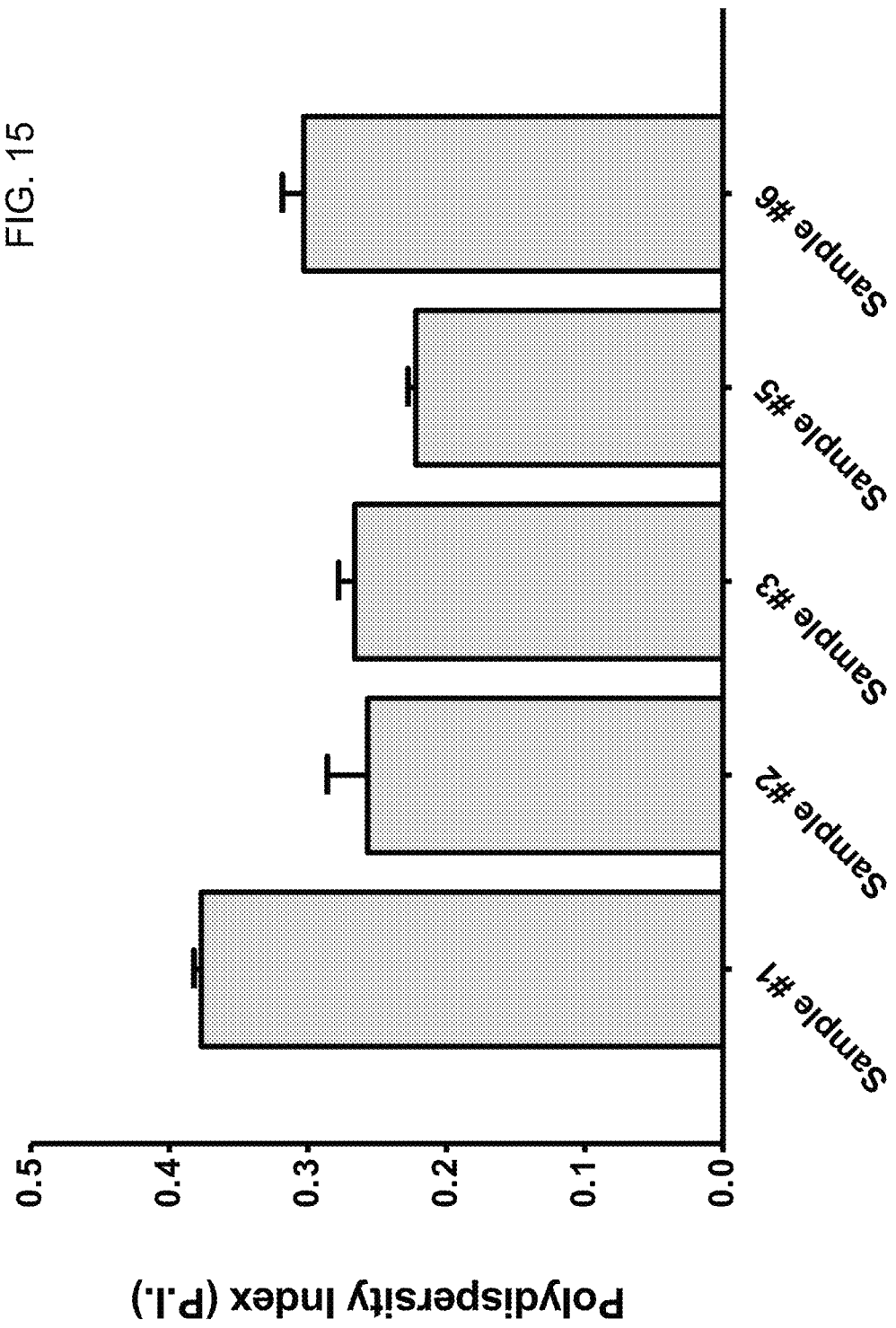
FIG. 15 is a bar graph of the zeta potential measurement the six samples of OC nano-emulsion in FIG. 13.

The newly formed emulsion using the self-emulsifying OC water extraction protocol was subjected to further characterization in terms of particle size analysis, zeta potential, and polydispersity index (FIGS. 13-15). The particle size is known to be a function of volume-weight distribution. The experimental results showed that the water extract of different EVOO samples in solution have excellent nano-system volume-weight distribution of 2.87 nm. The particle size similarity among the water extract of multiple EVOO samples from different sources clearly confirmed the self-emulsifying potential of OC in aqueous solutions (FIG. 13). To confirm the stability of the formed nano-emulsion, the zeta potential of each water extract sample has been determined (FIG. 14). Zeta potential serves as a reliable indicator of particle charge and emulsion stability. It reflects the potential difference between the dispersion medium and the stationary layer of fluid attached to the dispersed particle. Nearly all samples were found to have zeta potential higher than 40 mV, suggesting that the self-emulsified OC in water is a highly stable nano-emulsion (FIG. 14). In order to evaluate the heterogeneity and correctness of particle size measurements, the polydispersity index (P.I.) was determined for each water extract sample (FIG. 15). The water extract showed an average P.I. of 0.3, suggesting the uniformity of the measured particle size and implying the lower susceptibility of the OC nano-emulsion to dispersion (FIG. 15). Overall, these results confirm the ability of OC crude water extracts obtained from different EVOO samples to form stable nano-emulsions in aqueous solutions. These OC water extracts still contain ~15% oleic acid, the major monounsaturated fatty acid in EVOO, which may also act as an emulsifying agent, facilitating the formation of a stable nano-emulsion.

Validation of the OC Water Extraction Method Using Different Sources of EVOO

In an attempt to validate the new water extraction method for OC from EVOO and confirm its reproducibility, the same water extraction protocol was adopted using seven EVOO samples from different sources. In addition, a corn oil sample was used as a negative control to evaluate the selectivity of the OC extraction protocol (FIG. 9). Quantitative $^1$HNMR as well as HPLC analyses was used for OC detection and quantification among different tested samples. Standard calibration curves were established using pure OC as an external standard (FIGS. 8E-8H) and the results are summarized in FIG. 9. The disclosed water extraction protocol was able to robustly extract OC from EVOO samples of different sources including Greece, Italy, and Florida, suggesting the protocol's efficiency and reproducibility. OC quantitative results for each sample were reproducible upon using $^1$HNMR and HPLC analyses (FIG. 9). The Florida Olive Systems EVOO Sample-4 as well as corn oil sample did not demonstrate any appreciable quantity of OC, even before the water extraction protocol. Upon water extraction, EVOO samples containing OC were subjected to further characterization of their emulsion properties including particle size, zeta potential, and polydispersity index (FIGS. 13-15). It was interesting to note that different tested samples were able to form stable nano-emulsions with similar particle size, zeta potential and polydispersity index values, suggesting the reproducibility of the OC extraction protocol and eliminating the possibility of any EVOO source-specific results for this method. Meanwhile, it is important to highlight that the extraction frequency and the used water volume will preferably correspond with the amount of OC content in each EVOO batch. Samples containing low to medium OC amounts will preferably use three to four extractions, but OC-rich EVOO samples (>80 mg OC/EVOO kg) will preferably have more than four extractions with water to ensure complete OC extraction. Using resin entrapment, as alternative to freeze drying, the extra water volume used for extraction cycles will not negatively affect the disclosed OC extraction process in terms of time, outcome purity, and cost effectiveness.

Stability of OC-Rich Nano-Emulsion

Figure 16:
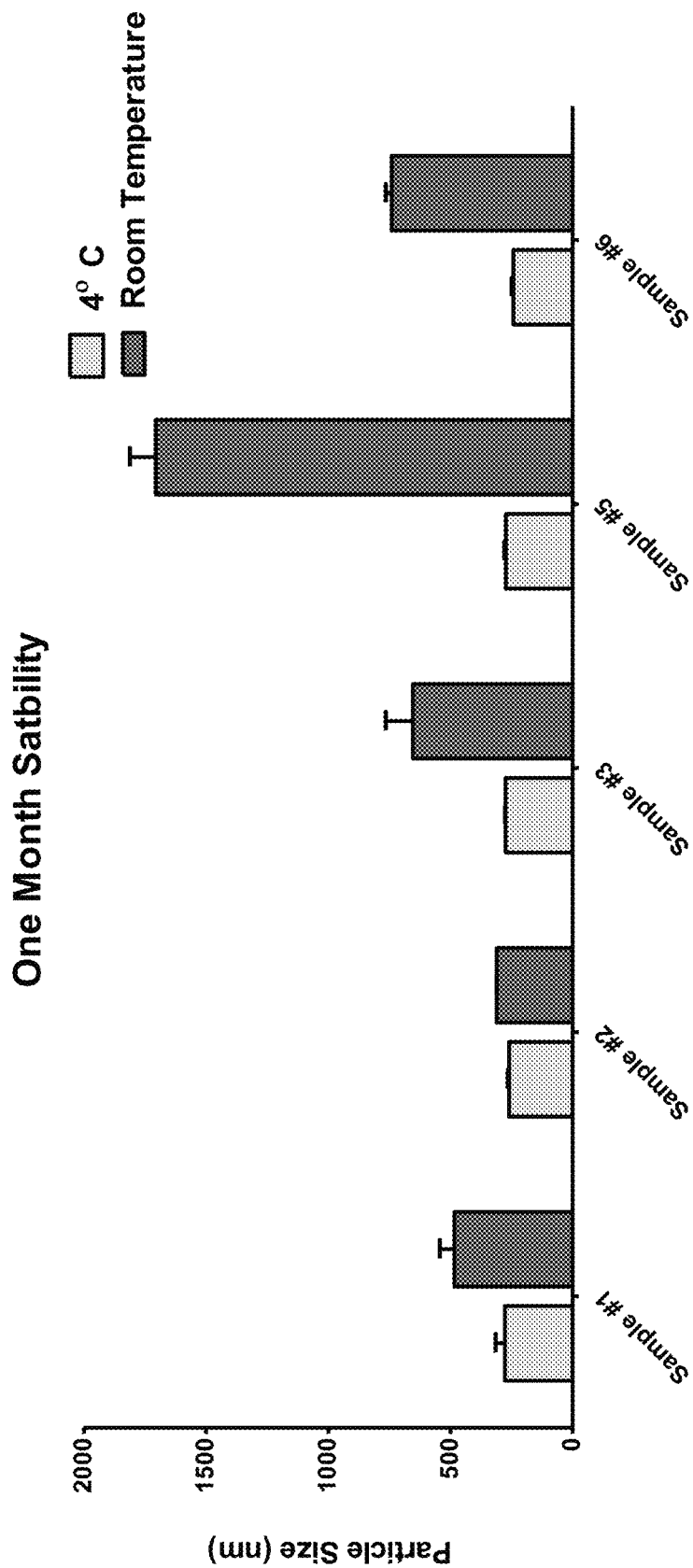
FIG. 16 is a bar graph of particle size measurements of the six samples of OC nano-emulsions in FIG. 13, with one part of each sample stored at room temperature for a month and another part of each sample stored at 4° C. for a month.
Figure 17:
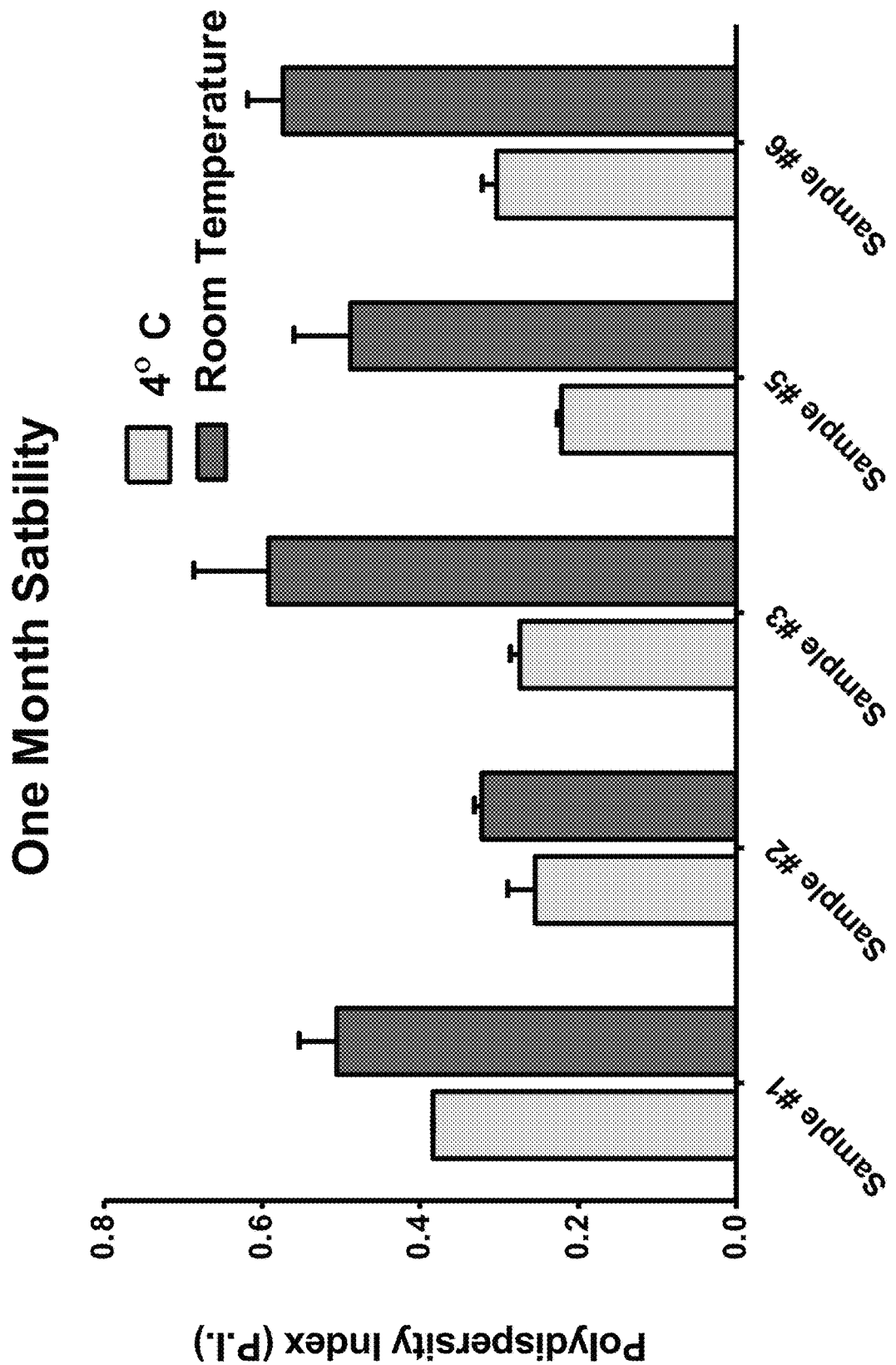
FIG. 17 is a bar graph of a polydispersity index for each of the one month stored sample parts of FIG. 16.
Figure 18:
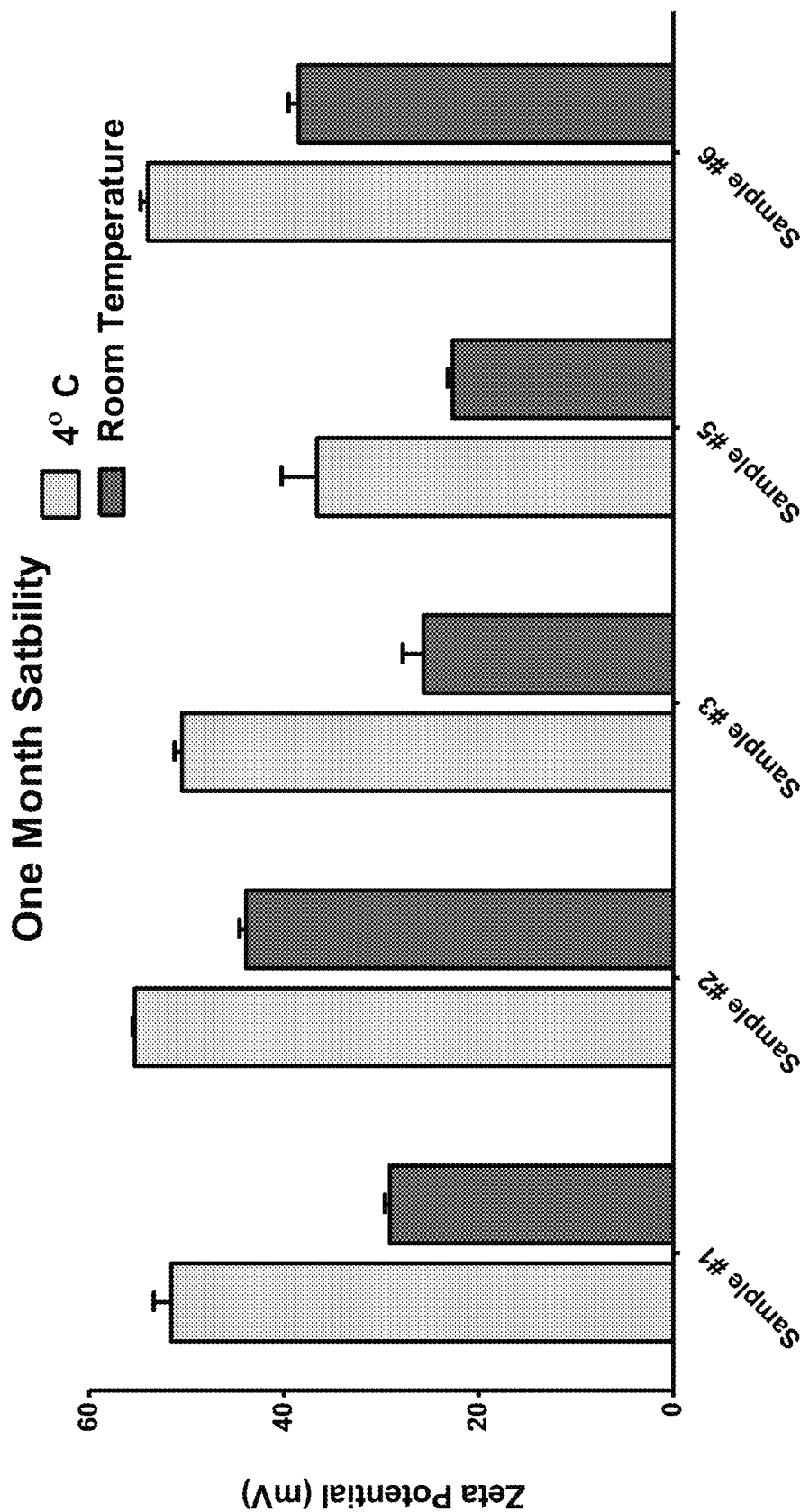
FIG. 18 is a bar graph of the zeta potential measurement for each of the one month stored sample parts of FIG. 16.

The stability of OC nano-emulsions from different EVOO sources were evaluated by $^1$HNMR analysis before and after storing each sample for one month at either room temperature or 4° C. In addition, particle size, zeta potential, and polydispersity index were determined for each OC nano-emulsion after one month to validate the $^1$HNMR results. The freeze-dried OC water extract preserved over nitrogen gas was 100% stable at room temperature for >6 months, as evidenced by its $^1$HNMR analysis. In contrast, OC-rich nano-emulsions tend to degrade within one month storage at room temperature, as shown by HPLC analysis (FIG. 9) and $^1$HNMR analysis. Consistently, OC-rich nano-emulsion stored at room temperature for one month revealed a significant drop in zeta potential along with a concomitant increase in particle size and polydispersity index in all investigated EVOO samples, suggesting the instability and possible degradation of OC nano-emulsion at room temperature within days (FIGS. 16-18). On the contrary, the refrigerated OC nano-emulsion samples at 4° C. showed a better stability profile than those stored at room temperature, with no significant changes in zeta potential, particle size, and polydispersity index compared to their respective initial values before storage (FIGS. 16-18). Consistently, HPLC analysis showed that refrigeration slowed degradation of OC in the refrigerated nano-emulsion samples compared to samples stored at room temperature (FIG. 9). Overall, this stability experiment suggests that OC nano-emulsions are less stable at room temperature and may degrade within days, while their stability is improved upon storage at 4° C. for one month while the freeze-dried OC extracted by water method can be stored frozen under nitrogen for longer than six months. The freeze-dried or resin-purified OC-rich dry extract can be freshly reconstituted in appropriate water volume to form, for example, a value-added Oleocanthal Water product that can be consumed by humans for a condition of improved health and prevention of cancers and Alzheimer's disease as it correlates with the OC's biological activities. The stability of the OC self-nano emulsion can be further enhanced in future with, for example, the use of food-approved surfactants.

Effect of OC Nano-Emulsion on Breast Cancer Cell Proliferation

Figure 19:
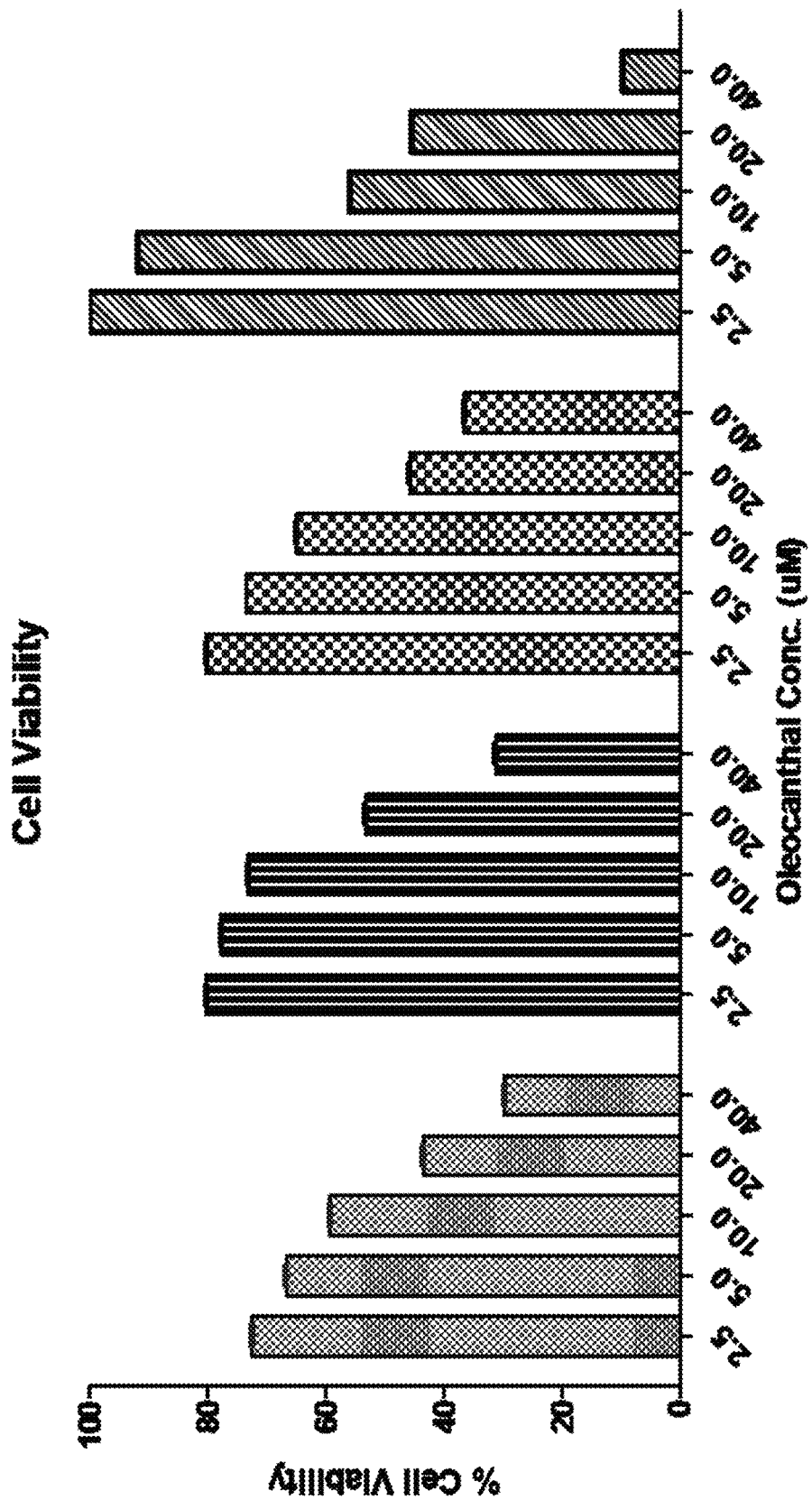
FIG. 19 is a bar graph showing the effect of OC nano-emulsion on different c-Met-dependent BC MDA-MB-231, MDA-MB-468, BT-474 and MCF-7 cells after 72 h treatment period, compared to vehicle control. Viable cell count was determined using MTT assay. Cells were plated at a density of 1×10$^4$ cells/well in 96-well plates and maintained in media supplemented with 10% FBS and allowed to adhere overnight. Next day, cells were washed with PBS, divided into different treatment groups. Cells were fed fresh treatment media every other day for the 72 h treatment period. Viable cell count was determined by MTT assay. Vertical bars indicate the mean cell count ±SEM in each treatment group, n=3/treatment dose. *P<0.05 as compared with vehicle-treated controls.
Figure 20:
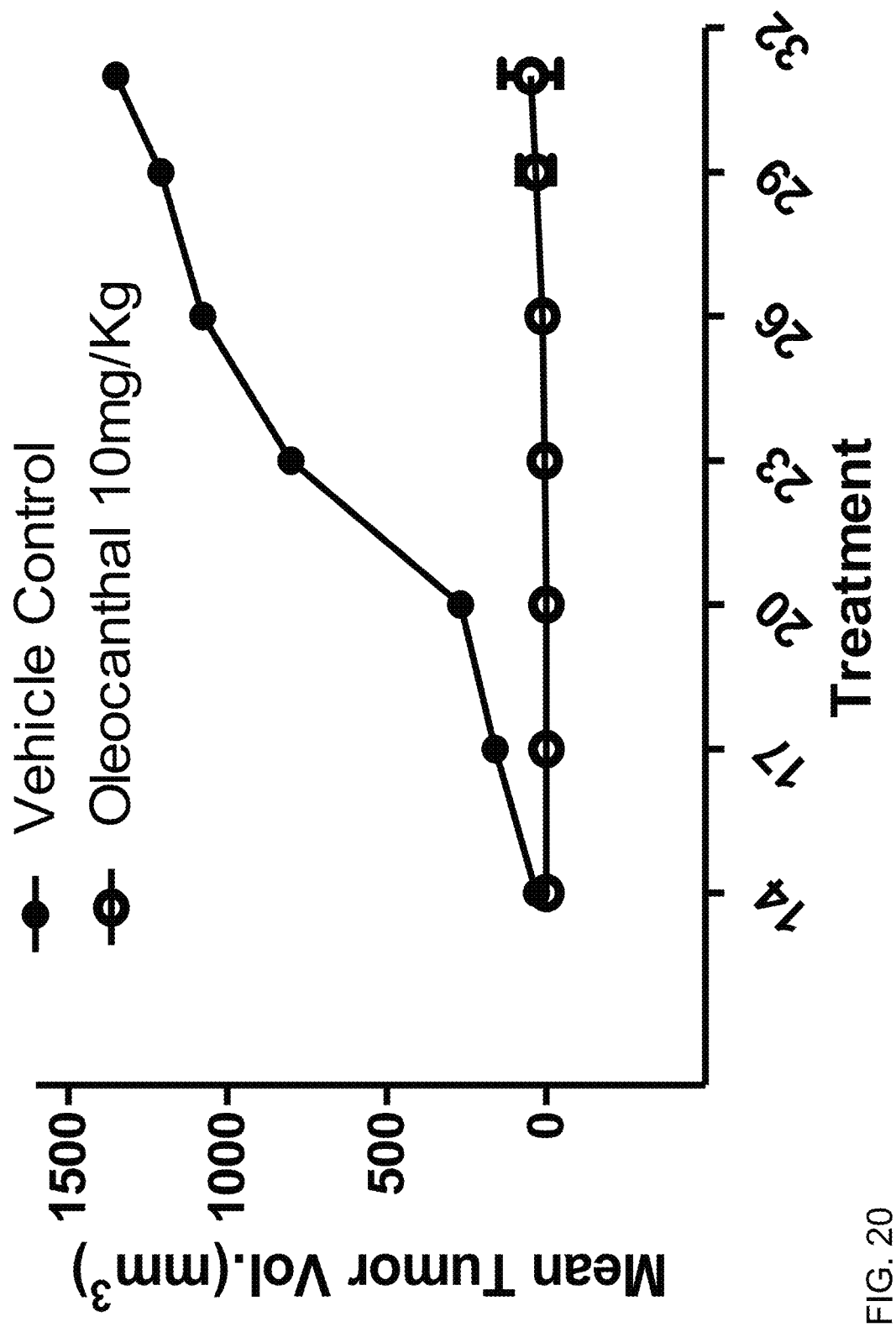
Figure 22:
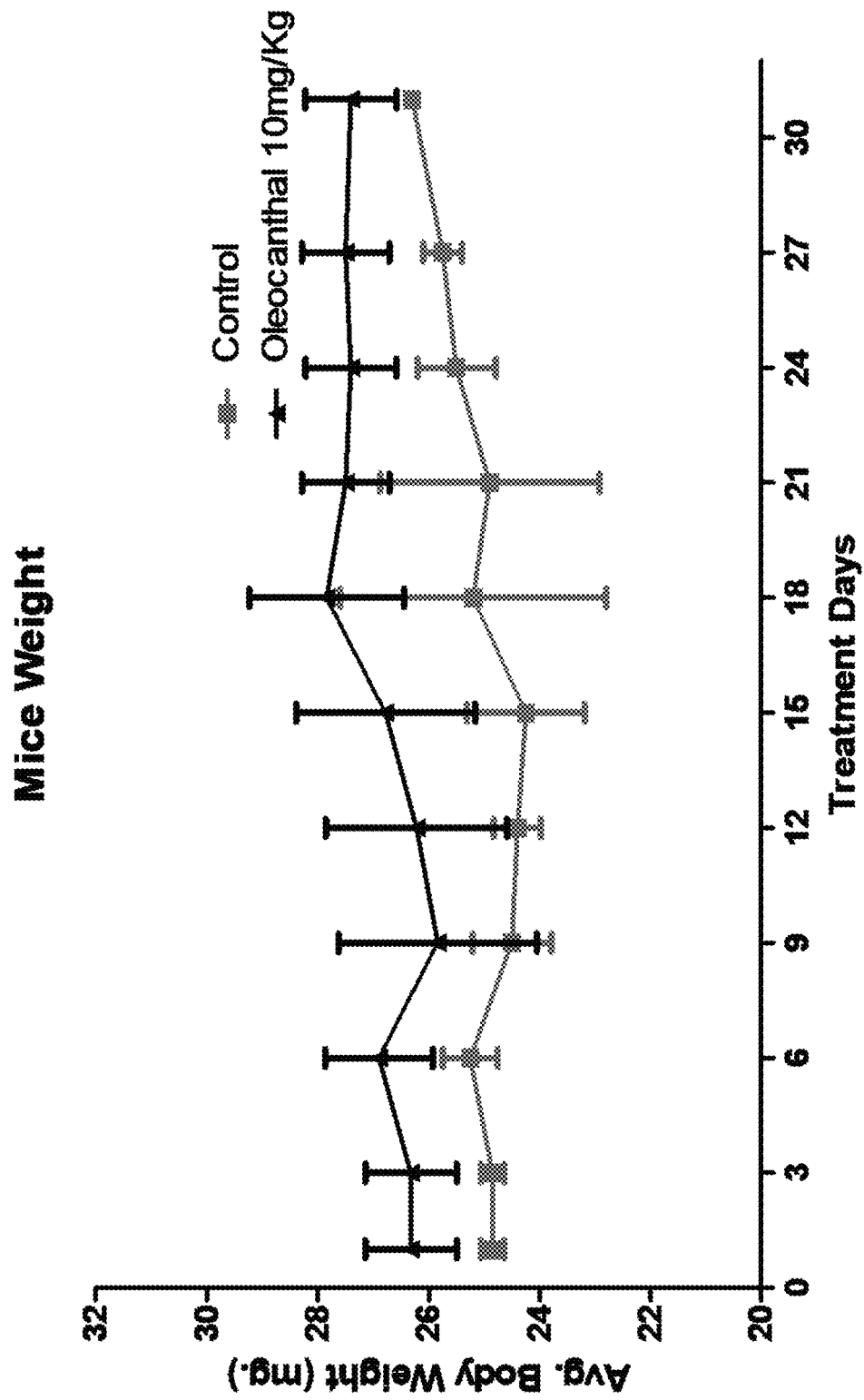
Figure 23:
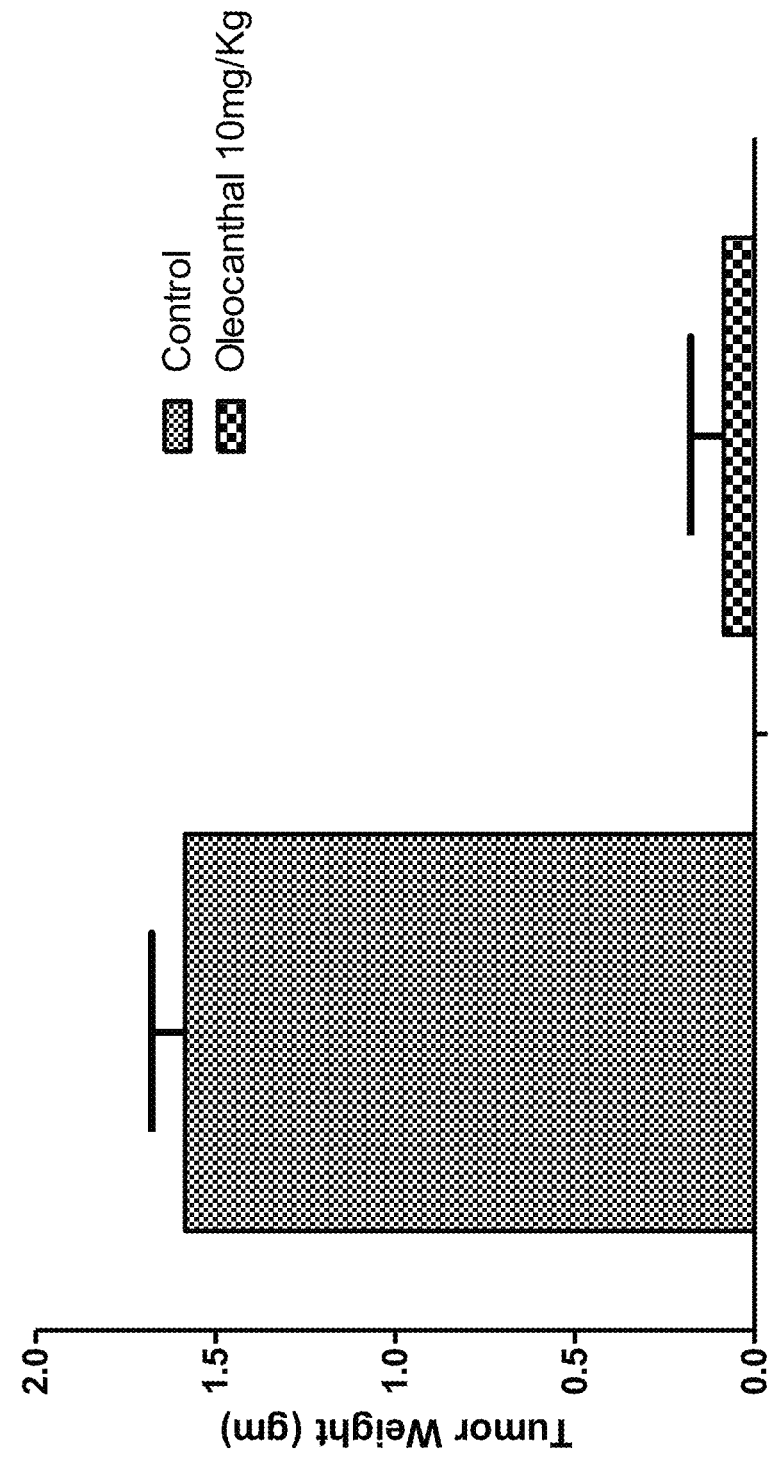

OC nano-emulsions were assessed for ability to inhibit the proliferation of key human BC cell lines using the MTT assay. The cell lines have been selected to represent different BC phenotypes. The triple negative MDA-MB-231 and MDA-MB-468 BC cells lack the expression of estrogen receptor (ERα), an important target for human BC therapy, while they overexpress c-Met, a well-established receptor tyrosine kinase that mediate BC survival and motility and known to be the molecular target of OC in BC. In contrast, MCF-7 and BT-474 breast cancer cells express ERα and c-Met, however, the latter is expressed at relatively lower levels compared to the triple negative BC cells. The antiproliferative effects of different doses of OC nano-emulsion on the growth of MDA-MB-231, MDA-MB-468, MCF-7, and BT-474 BC cell lines after 48 h culture period are shown in FIG. 19. Treatment with OC nano-emulsion dose-dependently inhibited the proliferation of the four BC cell lines (FIG. 19). The OC nano-emulsion was more potent against the most c-Met-dependent MDA-MB-231 triple negative BC cells compared to the other three cell lines. The IC50 values for OC nano-emulsion were 19.4, 25.2, 24.4 and 20.1 μM in MDA-MB-231, MDA-MB-468, BT-474, and MCF-7 cells, respectively (FIG. 19). It is worth mentioning that: 1) there is an urgent need to develop new treatments for the aggressive triple-negative BC subtypes, which currently lack targeted therapy, conferring an additional advantage to the proposed OC nano-emulsion; and 2) despite its modest in vitro activity, OC shows significantly potent in vivo activity that may even compare to standard chemotherapy. The results clearly indicated that OC nano-emulsion nearly maintained the antiproliferative activity of pure OC against the same BC cell lines, suggesting the potential of this nano-emulsion as future dietary chemopreventive and/or chemotherapeutic supplement and/or post tumor removal therapeutic.

In Vivo Oral Antitumor Activity OC Nano-Emulsion Against TNBC

Previous experiments of the inventors showed that intraperitoneal administration of 5 mg/kg of pure OC, 3×per week showed 65% tumor growth inhibition in the triple negative breast cancer (TNBC) MDA-MB-231 xenograft in female athymic nude mice. Those results suggest increased OC potency when used in early rather than late treatment modes.

Turning to FIGS. 20-23, in the current disclosure, as a future dietary candidate OC nano-emulsion oral in vivo antitumor efficacy was assessed using the same mouse model using MDA-MB-231/GFP human BC cells. OC nano-emulsion was administered in preventive/early treatment mode orally at 10 mg/kg every day, starting seven days before tumor cell inoculation and continued for 4 weeks. The mice were monitored by measuring body weight, and observation of their physical behavior throughout the study. Tumor progression was followed by direct measurement of tumor volume starting 14 days after the orthotopic tumor inoculation. Interestingly, the results demonstrated a significant reduction in both tumor volume and tumor weight of the OC nano-emulsion-treated group, compared to the vehicle-treated control group. The 10 mg/kg oral daily OC nano-emulsion treatments significantly suppressed the MDA-MB-231 tumor growth by 90% on the final day of study, compared to the vehicle-treated control group, without negatively affecting the treated mice's body weight or their behavior. The results indicated that the OC nano-emulsion demonstrates a robust antitumor efficacy via the oral route of administration, against BC in a clinically relevant orthotopic mouse model, which implies its oral bioavailability and tolerability as perspective dietary supplement to prevent invasive BC progression.

OC as BC Recurrence Inhibitor

Surgical excision of the early-stage confined tumors is a common clinical strategy used to minimize subsequent malignancy metastasis, which pose life-threatening hazard to patient. The relationship between primary tumor and subsequent metastasis is not fully understood. Nearly 4-10% of newly diagnosed BC patients have concurrent metastatic disease. Oversimplifying metastasis as migration of cells from primary to target organs is lacking the in-depth needed to prevent cancer spread. The "diaspora," people scattering away of established homeland, concept was proven applicable to metastasis. The metastatic sowing is associated with late primary tumor growth and invasion phases but recently systemic dissemination was shown to be an early event. Similarly, tumor directional spread from primary to secondary sites was shown to be complicated and dynamically interacting. Therefore, primary and secondary tumors may both grow linear/parallel and spread to distant organs, or bidirectional metastatic re-seeding to the original primary tumor site may occur, inducing recurrence.

Development of early detection tools aided to classify primary tumor stage and subsequent presurgical (neoadjuvant) or postsurgical (adjuvant) treatments to minimize metastatic potential. Numerous BC patients develop chemoresistance resulting in chemotherapy-resistant recurrence. Subsequent to chemotherapy use, apoptotic cell death should be the best expected tumor cell response. However, tumor cells may stay viable after the chemotherapy through cellular senescence and cytoprotective autophagy, generating secretomes which can directly enhance the malignant phenotype. This challenge highlighted the need to target the non-apoptotic survival pathways to enhance chemotherapeutic efficacy and reverse or avoid this resistance to chemotherapy.

The promising in vivo activity of OC nano-emulsion against TNBC and extensive preliminary results showing its activity as a c-Met activation inhibitor motivated the inventors' currently disclosed experiments to assess OC nano-emulsions' ability to prevent BC recurrence and extend recurrence-free durations after primary tumor surgical excision and extended use of neoadjuvant chemotherapeutics in a clinically relevant mouse model.

Oral OC Nano-Emulsion Inhibits TNBC Recurrence

Figure 24:
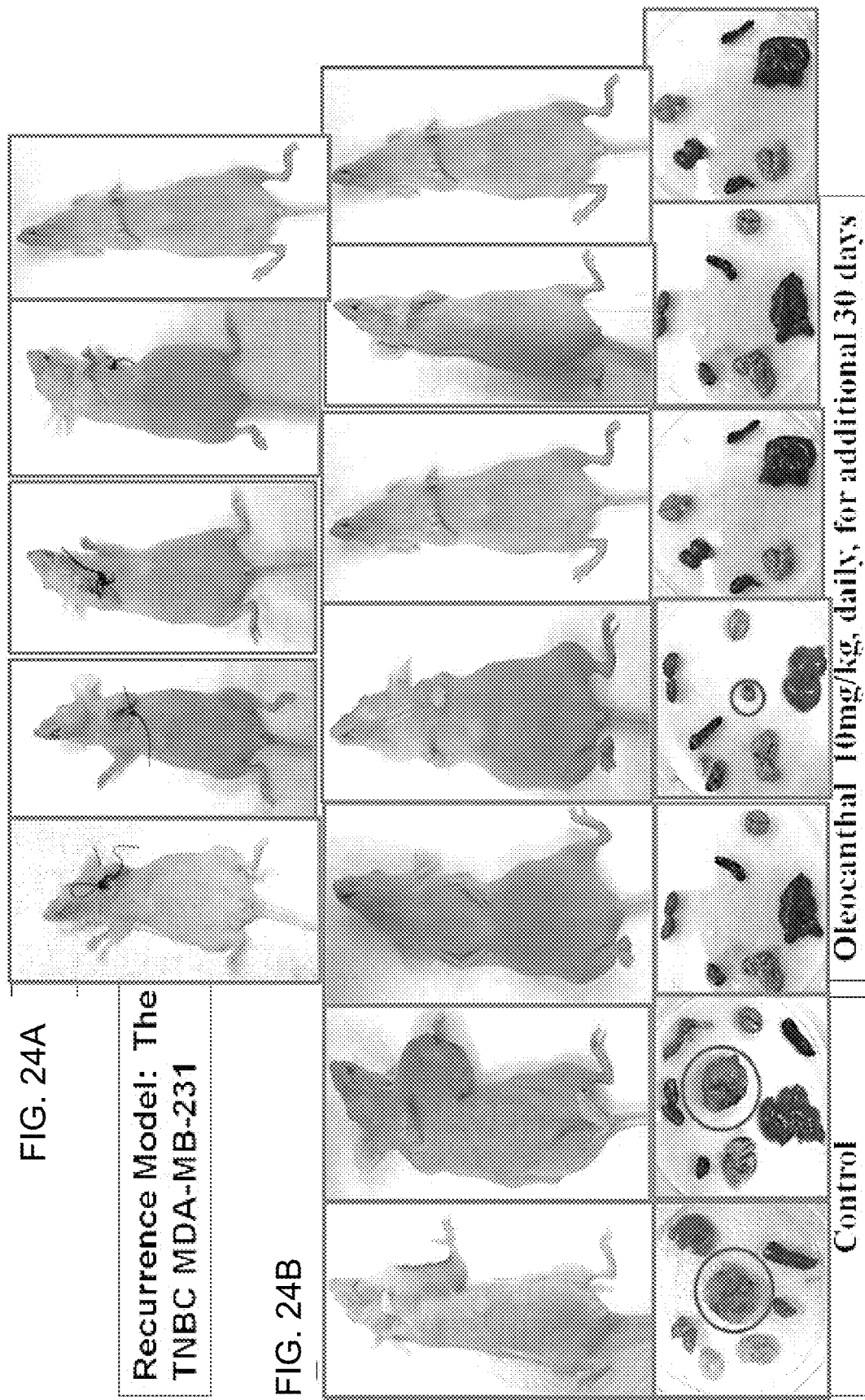
FIGS. 24A and 24B show oral OC nano-emulsion inhibits TNBC recurrence after primary tumor excision surgery.
Figure 25:
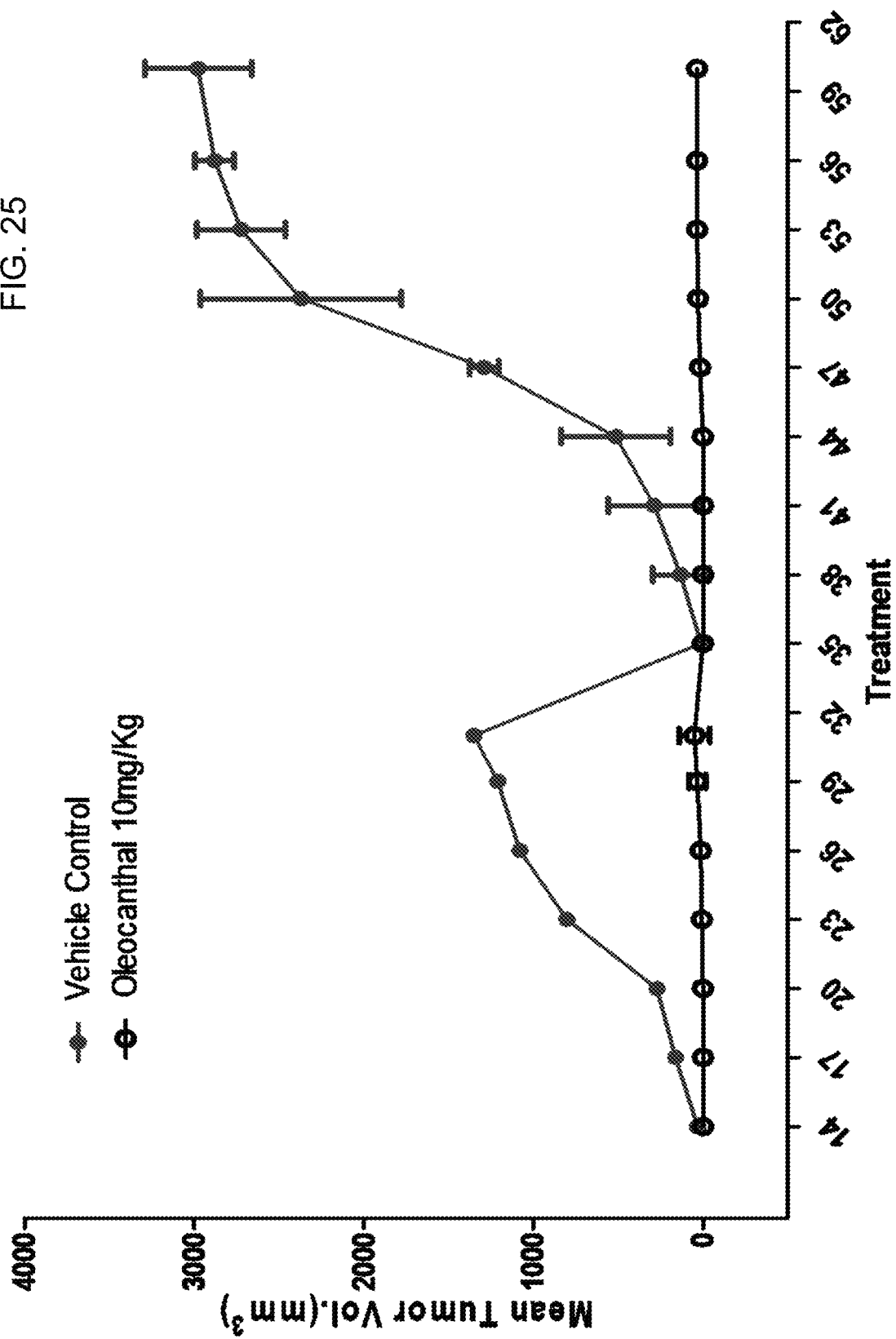
FIGS. 25-27 show OC oral nano-emulsion effectively inhibited TNBC recurrence without adverse effects on mice weight.
Figure 26:
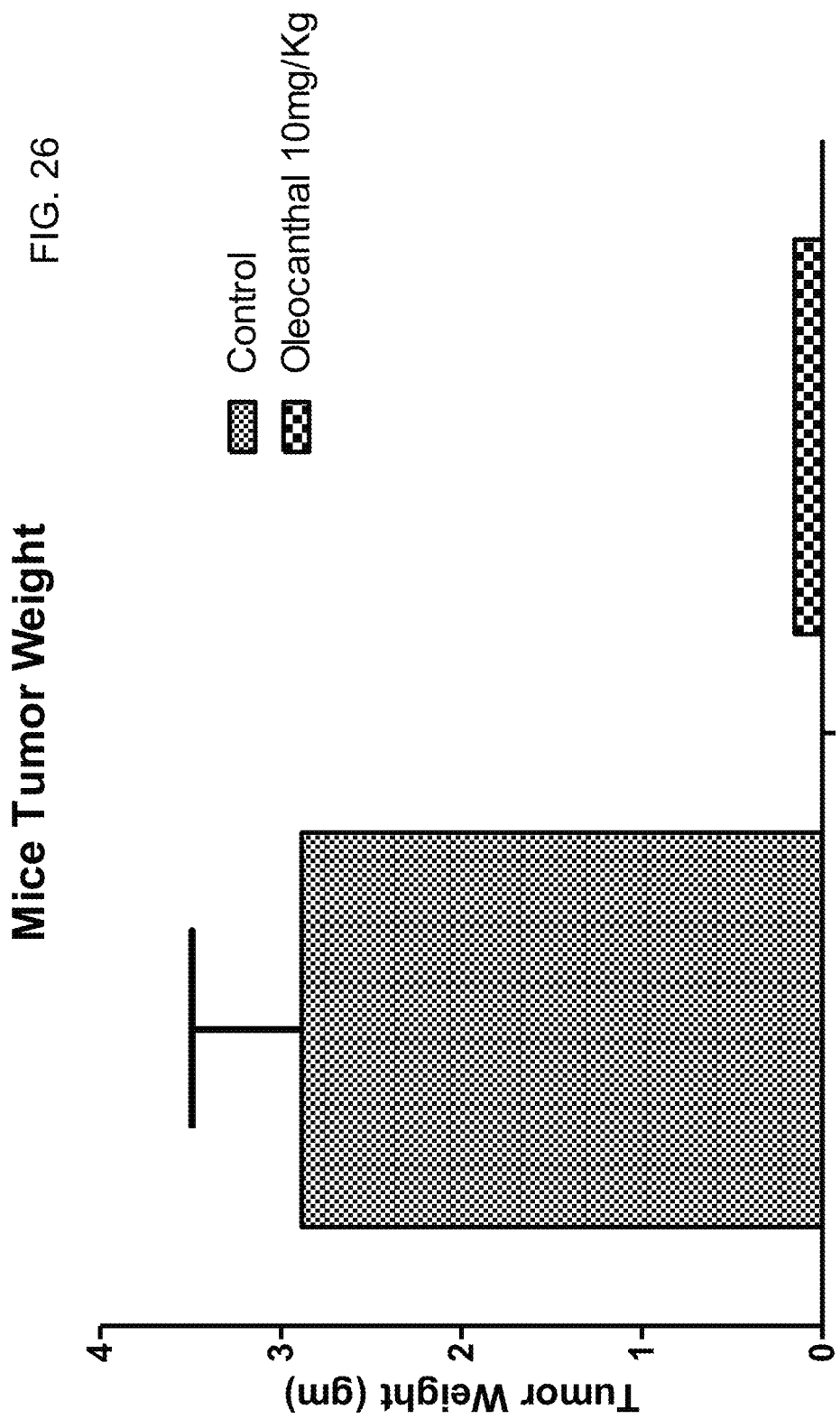
Figure 27:
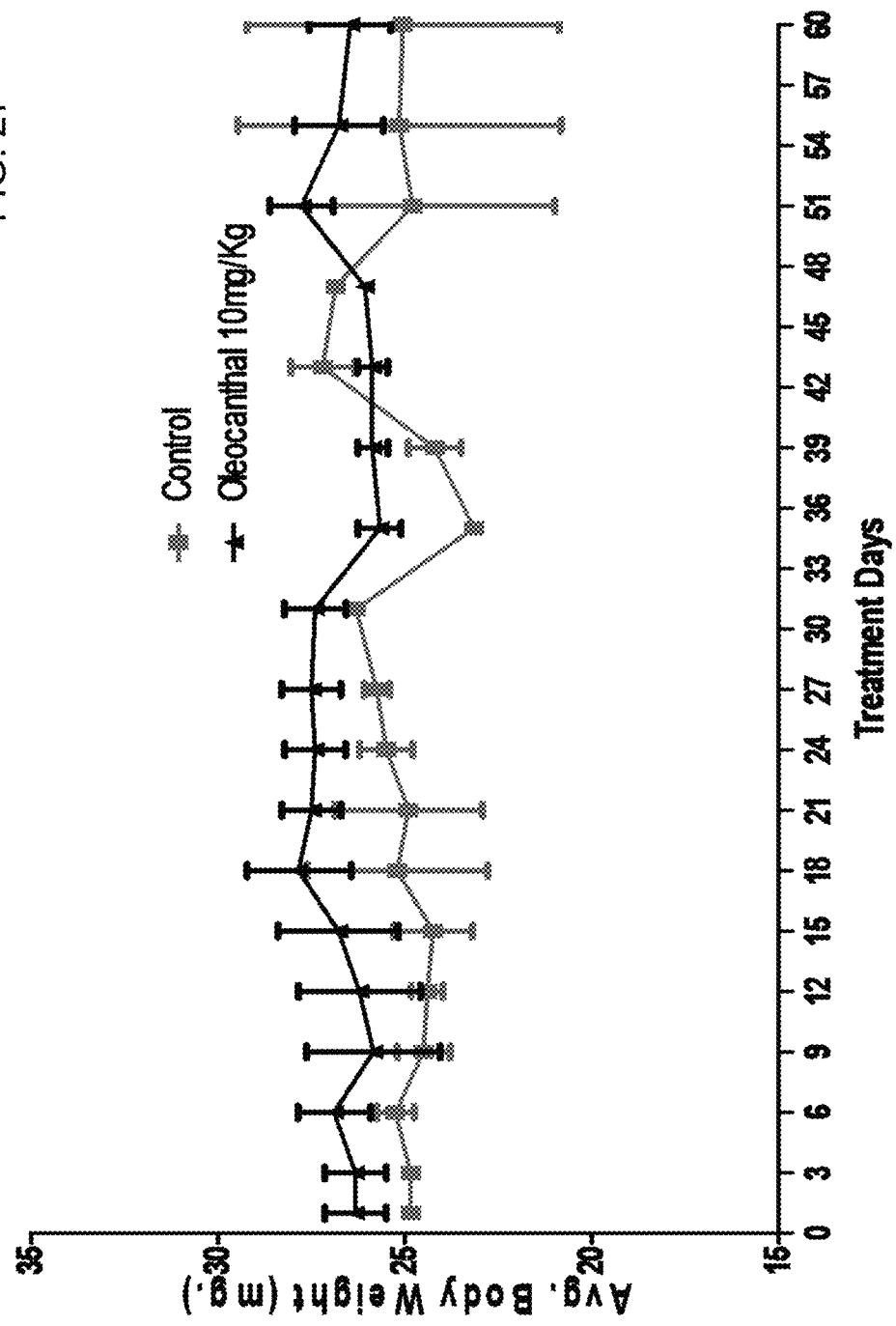

Turning to FIGS. 24A-27, the five mice used in the oral activity of OC nano-emulsion experiment were used for recurrence model. Since four out of these five mice developed tumors, these four animals were subjected to primary tumor excision surgeries on their 35th day of initial oral OC nano-emulsion treatment (FIG. 24A). OC nano-emulsion at 10 mg/kg, oral daily treatment continued for 30 more days and was compared with vehicle-treated control group (n=5). Only one of the five mice developed a small tumor, representing >95% TNBC recurrence inhibition (FIGS. 24B, 25, and 26). Treated mice showed neither changes in body or organs weight, morphology abnormality after sacrifice (FIGS. 24B and 27) nor behavioral changes.

OC Inhibits the HER2+/ER+ Breast Malignancy Growth In Vivo

Figure 30:
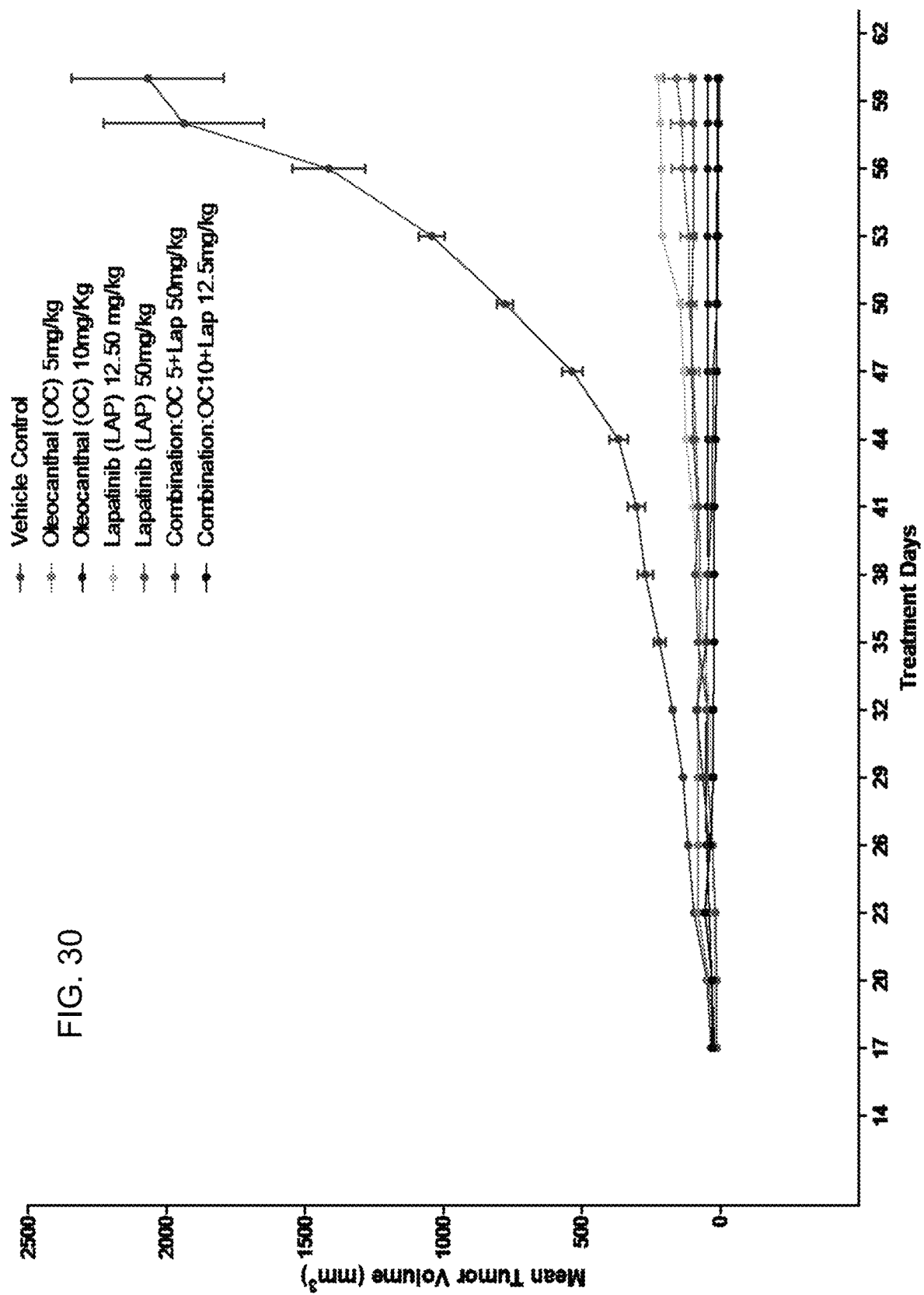
Figure 31:
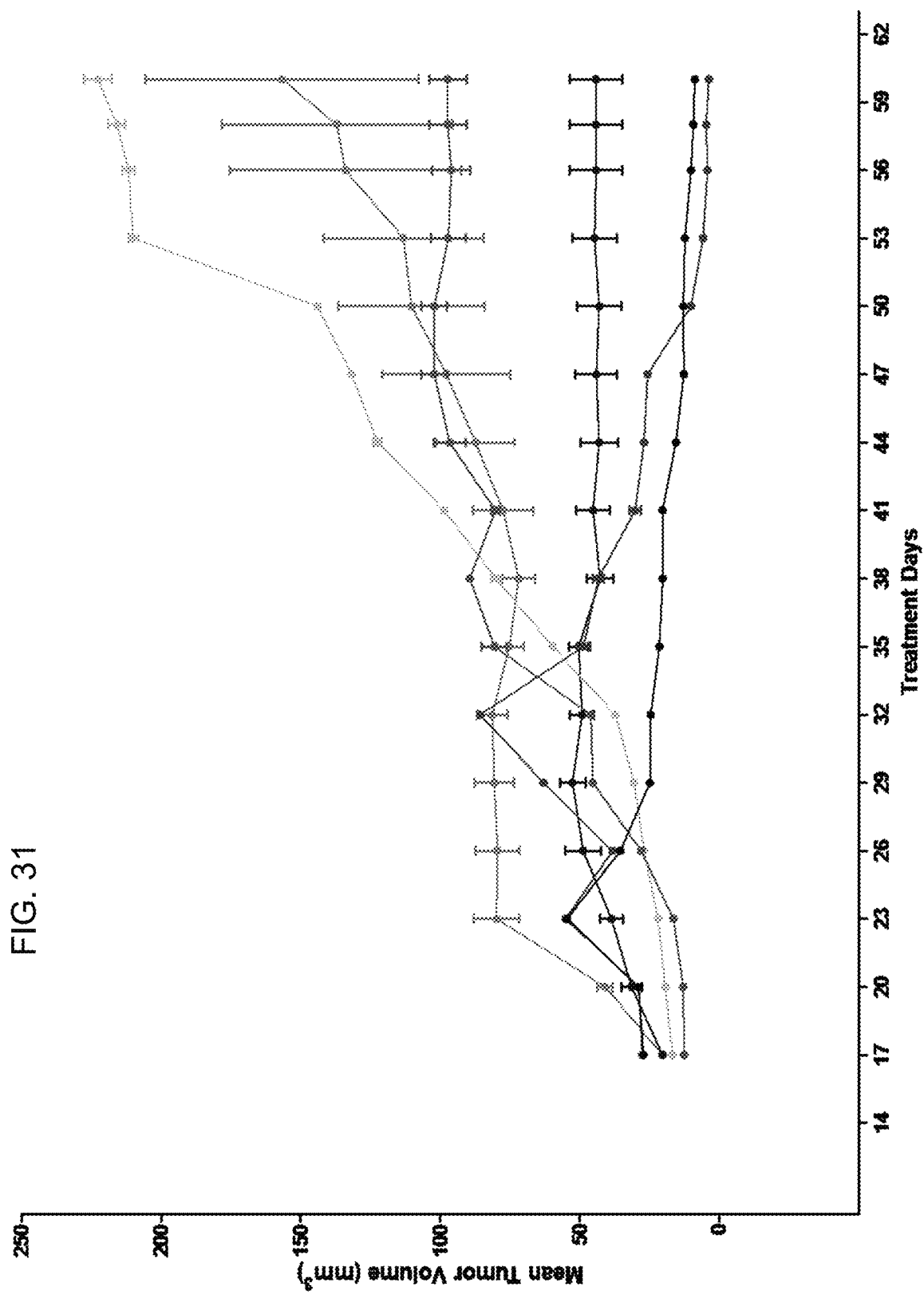
Figure 32:
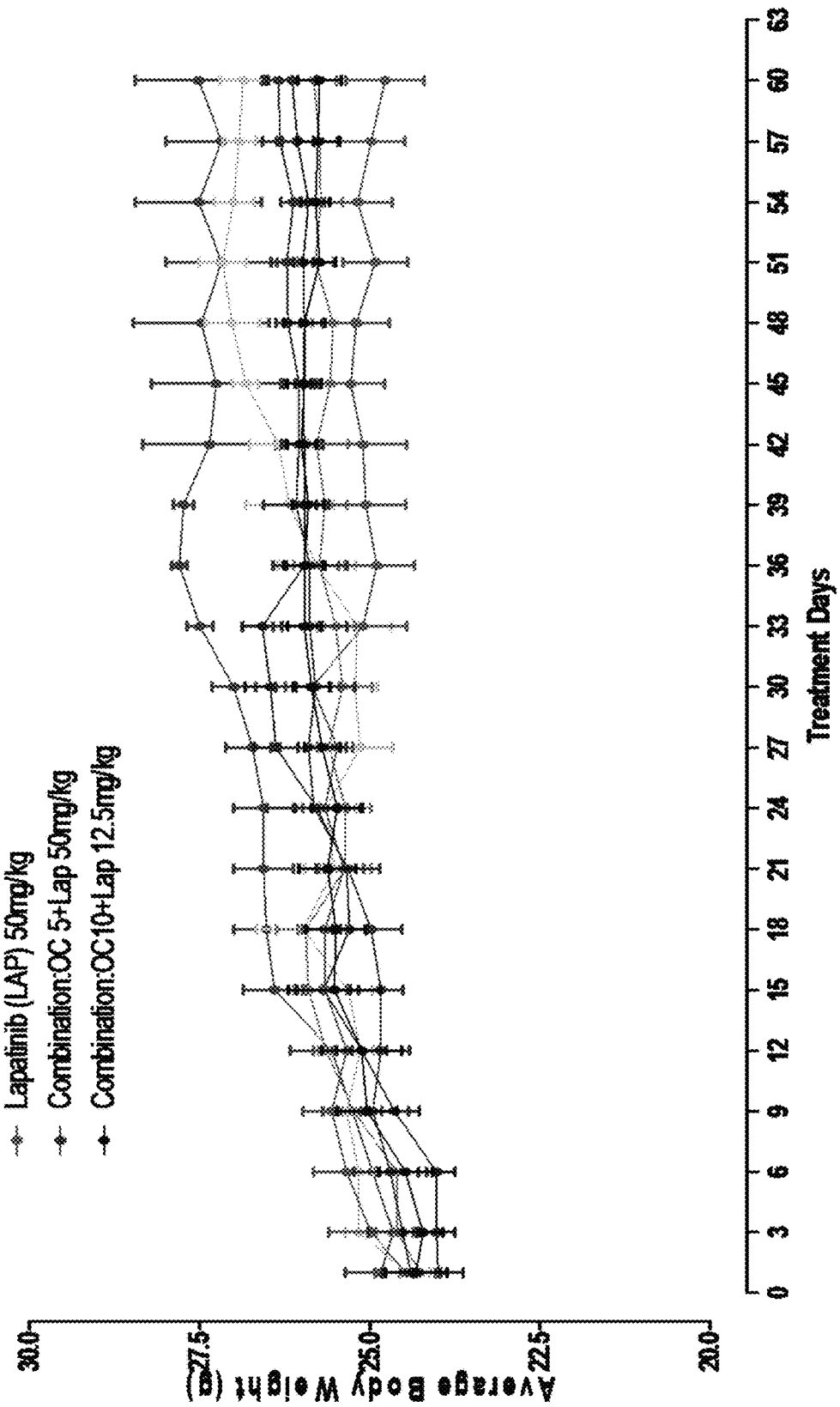

Turning to FIGS. 28A-32, the HER2+ BC represents >15% of total BC cases with aggressive metastatic and highly resistant profile. To expand the scope of in vivo OC nano-emulsion activity against various BC, the inventors tested OC activity in vivo in nude mouse model at two different doses, 5 mg/kg and 10 mg/kg, 3×/week, intraperitoneal for 60 days. Both OC doses were significantly and dose-dependently able to inhibit 88.2% and 93.2%, respectively, of the in vivo HER2+/ER+BT-474 tumor weight in nude mice (FIGS. 28A-28C), compared to vehicle-treated control groups. Both OC doses showed superior BT-474 tumor weight and volume inhibition compared to 12.5 mg/kg and 50 mg/kg lapatinib (FIGS. 29-31). Both doses did not significantly change the tested animals' body weight over the 2-month treatment period (FIG. 32). It is worth noting that the standard dual HER2-EGFR kinase inhibitor lapatinib at 12.5 and 50 mg oral doses, 5×/week, were inhibiting 85.9% and 89.9% of BT-474 tumor growth in the same mouse model, and that both combined OC 5 mg/kg lapatinib at 50 mg oral dose and combined OC at 10 mg/kg and lapatinib at 12.5 mg/kg performed best of all (FIG. 29), suggesting synergistic effect of OC and the kinase inhibitor in combating cancer cell growth.

Figure 33:
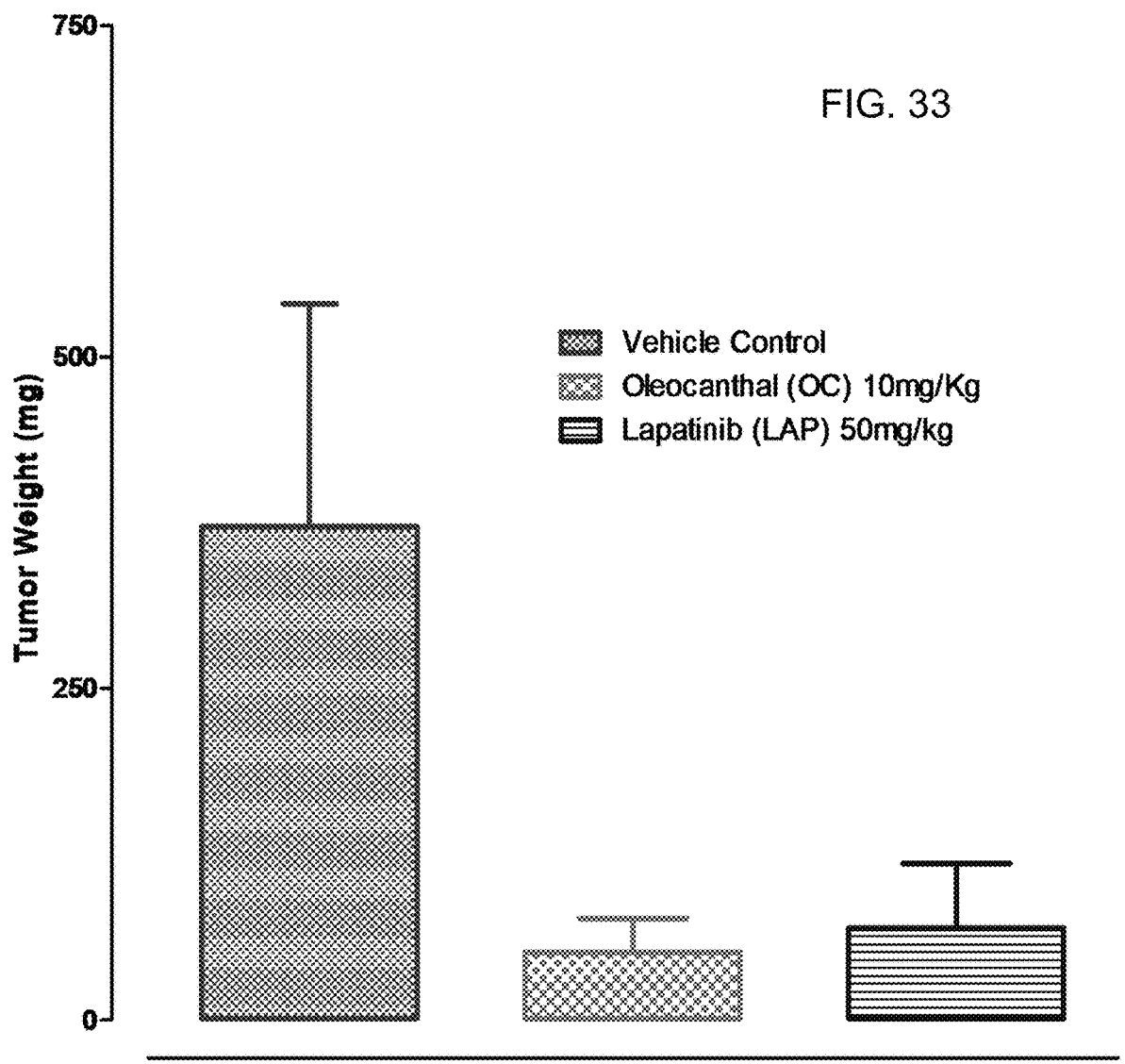
FIGS. 33-35 show OC inhibits the HER2$^+$-ER$^+$ breast malignancy recurrence in vivo after a primary tumor excision conducted at day 60.
Figure 34:
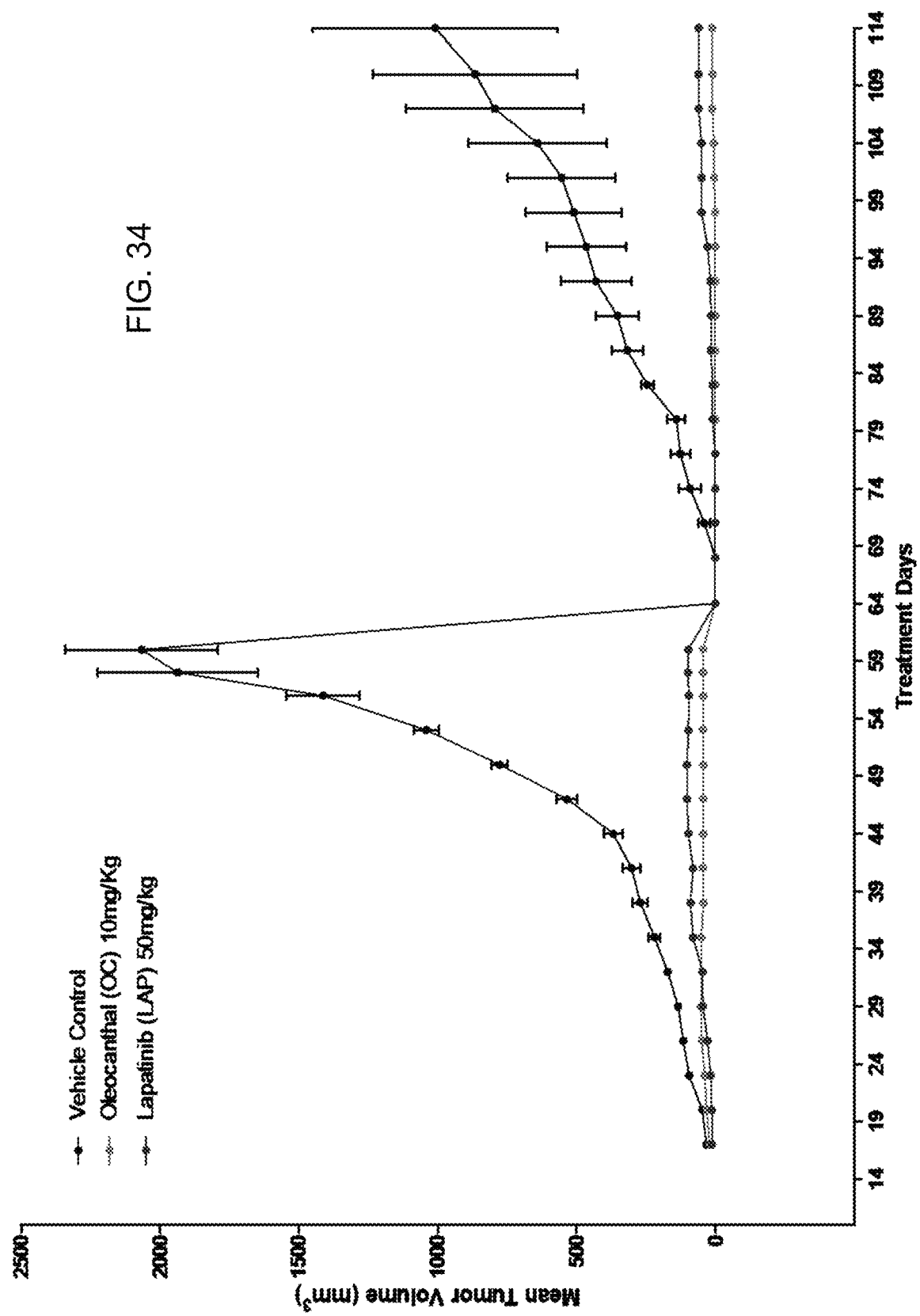
Figure 35:
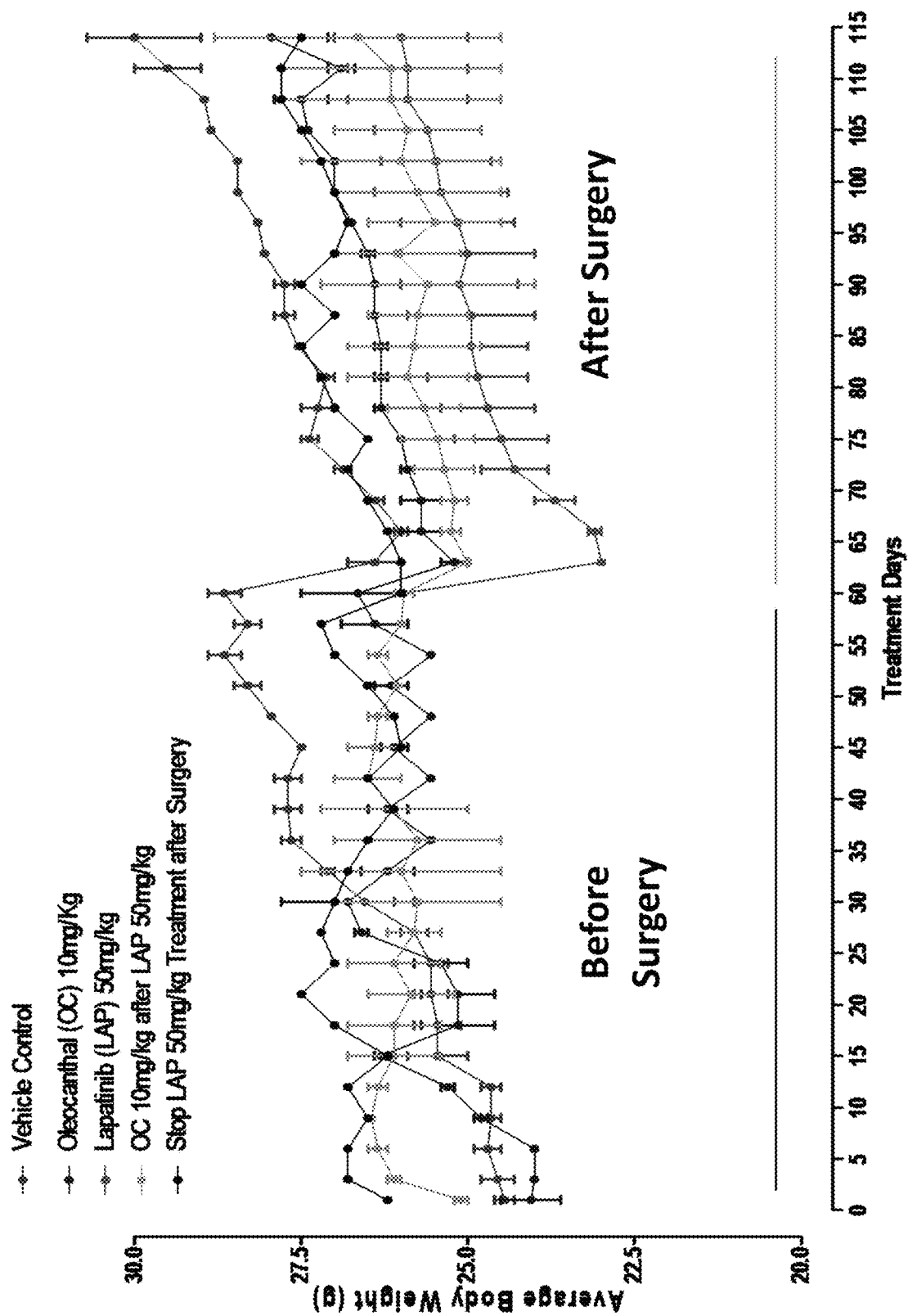

OC Inhibits the HER2+/ER+ Breast Malignancy Recurrence In Vivo After Primary Tumor Surgical Excision Turning to FIGS. 33-35, animals treated with 60-days treatment OC in previous experiment were subjected to primary tumor surgical excision. OC at 10 mg/kg, ip, 3×/week treatment continued for additional 54 days more days and compared with vehicle-treated negative control and lapatinib (LAP) 50 mg/kg, 5×/week oral treatment as a positive control. OC inhibited 86.2% of the recurrence HER2+-ER+ tumor weight while lapatinib inhibited 81.4% of this tumor recurrence tumor weight (FIG. 33). Similarly, OC treatment showed significant recurrence tumor volume inhibition compared to lapatinib 50 mg/kg, 3×/week (FIG. 34). OC-Treated mice showed neither change in body or organs weight nor organ morphology abnormality after sacrifice unlike lapatinib-treated animals which showed significant weight decrease over the additional 54 days treatment period (FIG. 35). As shown in the chart, on day 114, the average body weight from highest to lowest, was vehicle control; OC 10 mg/Kg; LAP 50 mg/Kg that was stopped after day 60; LAP 50 mg/Kg until day 60 and then OC 10 mg/Kg until day 114; and the lowest was LAP 50 mg/Kg that was administered from the beginning until day 114.

OC Inhibits the TNBC and HER2+/ER+ Breast Malignancy Recurrence In Vivo After Completion of Paclitaxel and Lapatinib Neoadjuvant Regimen The correlation between c-Met/HGF pathway and tumor resistance is documented. OC 10 mg/kg, ip, 3×/week for additional 54 days inhibited the HER2+-ER+BT-474 BC cells recurrence after neoadjuvant lapatinib 50 mg/kg, 3×/week, regimen for 60-days (FIG. 36A-36C). Similarly, OC 10 mg/kg oral daily treatments effectively inhibited in vivo recurrence and reversed chemoresistance of the TNBC MDA-MB-231 BC cells to neoadjuvant paclitaxel. This was consistent with the OC c-Met inhibitory activity and previously shown growth and recurrence effects.

Conclusion

Oleocanthal has shown to be an exceptional in vivo bioactive EVOO-derived natural product. It will become sooner or later a drug and/or commercial dietary supplement to control and prevent cancer, neurodegenerative and inflammatory diseases. The unique chemistry of OC made its isolation very challenging and therefore there is a dire need to find a cost-effective reliable isolation method to fulfill the future expected market need. The present disclosure establishes novel OC isolation methods. The proposed protocols have demonstrated, for example, the successful capacity of water for extracting OC from EVOO leading to the discovery of a novel value-added OC-containing food product. The results encourage water extraction as both environment friendly, green chemistry and highly efficient alternative to all other organic solvents for the OC large-scale extraction. An important advantage of this method is maintaining the remained EVOO after OC extraction for commercialization to consumers who will prefer to use EVOO without pungency or bitterness. The disclosed small-scale short-term stability study provided preliminary insights regarding the stability of the OC emulsion and suggests its reconstitution preferably immediately before use, or combination with appropriate chemical stabilizers. The dried OC-rich residue resulting from this method, which is stable at room temperature for extended periods, can be reconstituted in water at a dose equivalent to the average of natural OC occurrence in EVOO, 100 mg/L, to make a value-added "Oleocanthal Water" or may be administered in orally in pill form both dry and/or in a liquid capsule, for example, at the same or higher concentrations, for public use for cancer control, including breast cancer, and chemoprevention and for people at Alzheimer's disease risk to improve cognition. In vitro and in vivo studies revealed the significant activity of the OC nano-emulsion as a novel inhibitor of the growth and recurrence of multiple invasive breast malignancies.

Materials and Methods

Chemicals and Reagents

All chemicals were purchased from Sigma-Aldrich (St. Louis, Mo.), unless otherwise stated. (-)-Oleocanthal was isolated from EVOO using the water extraction method similar to that described under sample preparation section. Methanol, acetonitrile, dichloromethane and ethyl acetate were purchased from VWR (Suwanee, Ga.). Deionized water was obtained from an ultra-purification system at the University of Louisiana at Monroe.

Extra-Virgin Olive Oil Samples

The EVOO samples used in the study were either generously provided by Florida Olive Systems, Inc. or commercially available and purchased from Sam's Club and Brookshire chains at Monroe, La. Samples of eight different varieties including Florida Olive Systems samples and commercially available (Brookshire: L183TE-241, L245TE-241 and Sam's Club Daily Chef: LO22RE-565, Table 1) were included in the study. Most of the commercially available EVOO origin was Italy. Olive oil production was performed on either two-phase or three-phase mills. All samples were provided by small-scale producers that could guarantee their monovarietal origin.

General Experimental Procedures

TLC analysis was carried out on precoated Si gel 60 F254 500 µm TLC plates (EMD Chemicals), using n-hexane-EtOAc (8:2) as a developing system. For column chromatography, Sephadex LH-20 (Sigma Aldrich, bead size 25-100µ) was used with isocratic dichloromethane as a mobile phase. 1% vanillin in concentrated H2SO4 was used as a visualizing reagent. 1H and $^{13}$CNMR spectra were recorded in CDCl3, using tetramethylsilane (TMS) as an internal standard, on a JEOL Eclipse-ECS NMR spectrometer operating at 400 MHz for 1H NMR and 100 MHz for $^{13}$CNMR. High performance liquid chromatography (HPLC) analysis was conducted using Simadzu HPLC system equipped with a variable wavelength UV/Visible detector set to 230 nm. Generally, 1:100 ratios of mixtures to be chromatographed versus the used stationary phase were used in all liquid chromatographic purifications.

Reference Compounds

S (-)-Oleocanthal (OC) was isolated from extra-virgin olive oil (>95% purity) to be used as an external standard in quantitative studies. Separation was performed on a Phenomenex Cosmosil 5C18-AR-II column (250 mm×4.6 mm, 5 µm; Phenomenex Inc., Torrance, Calif.) at 25° C. Isocratic elution was performed using H2O-CH3CN (6:4) as a mobile phase. A flow rate of 1 mL/min, injection volume of 25 µL, and 1 mg/mL sample concentration were used. The identity of OC was undoubtedly defined by extensive 1D and 2D NMR analysis and comparison of its 1H and $^{13}$C NMR data with literature. Pure OC sample was kept frozen in amber glass vial under $N_2$ gas.

EVOO Extraction and Sample Preparation

Acetonitrile Extraction Method

About 100 mL EVOO (B #LO22RE-565, Italy) and 100 mL CH$_3$CN were mixed in a 500 mL separating funnel, vigorously shaken, and allowed to separate (FIG. 2). The process was repeated for two additional times; each using 100 mL CH$_3$CN. The organic acetonitrile layers were combined in a Pyrex 1 L flask and subjected to ultra-freezing for 1.5-2.5 h at −80° C. The mixture was then immediately filtered on a Whatmann #1 filter paper. Ultra-freezing was repeated for two additional times followed by filtration to afford clear oily solution containing OC. This oily solution was then dried and subjected to further purification using lipophilic Sephadex LH-20.

Water Extraction Method

EVOO (100 mL) was mixed with de-ionized water (5×150 mL) in a 500-mL separating funnel, vigorously shaken for three times (though three is preferable, more or less times shaking are also anticipated), and allowed 10-15 min for phase separation (longer phase separation is possible, including 20, 30, 45, and 60 min.). The lower aqueous layers were combined and subjected to ultra-freezing for around 30-60 min at preferably −80° C. (temps from, for example, −100° C. to −60° C. are also anticipated). The aqueous extract was then preferably immediately filtered on a Whatmann #1 filter paper followed by freeze drying until preferably complete dryness (FIG. 5). To render the process time and cost-effective, freeze drying was replaced with a wet-packed column using 45 g Sorbtech (Sorbent technology Sepabeads resin Styrenic adsorbent, Sp-70-01) (Scheme 3). The column was washed with 150 mL water and then eluted with 300 mL acetone. The acetone eluate rich in OC was collected and dried. Meanwhile water eluent was subjected to shake with CH$_2$Cl$_2$ followed by collection of the CH$_2$Cl$_2$ fraction, evaporation under vacuum and $^1$H NMR analysis. Final OC purification was achieved by subjecting the dried acetone fraction to Sephadex LH-20 size exclusion chromatography using isocratic CH$_2$Cl$_2$ as a mobile phase. Eluted fractions were monitored using TLC analysis for the presence of OC.

q1H NMR Spectral Analysis

Figure 8A:
FIGS. 8A-8H are documentation of OC-water nano-emulsion isolation method.
Figure 8B:
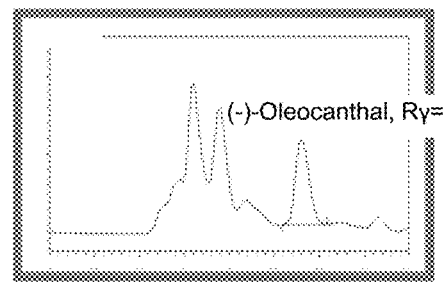
Figure 8C:
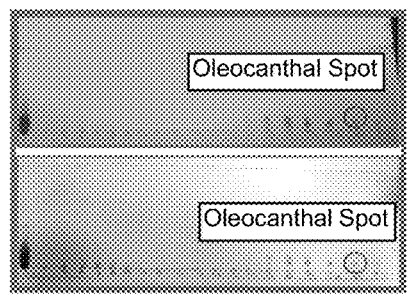
Figure 8D:
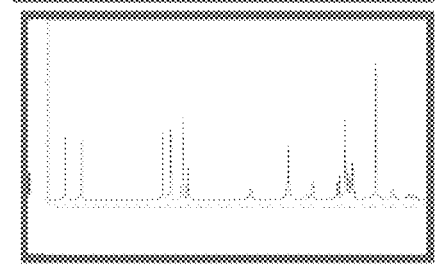
Figure 8E:
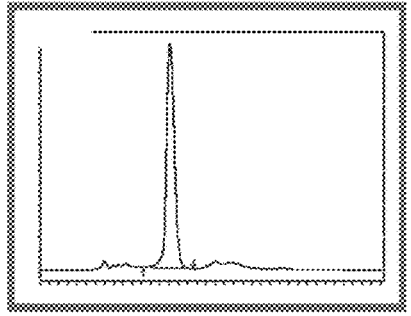
Figure 8F:
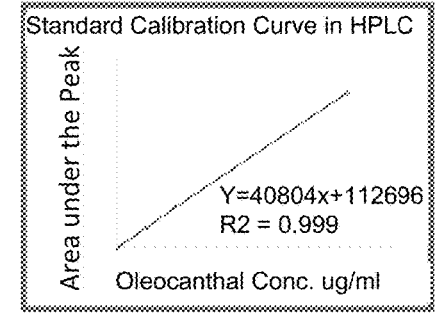
Figure 8G:
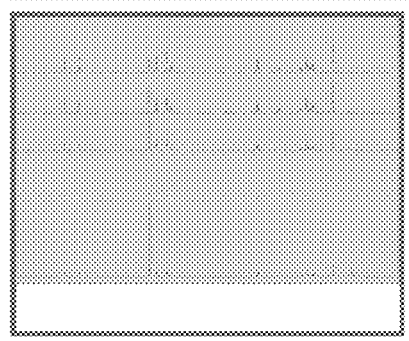
Figure 8H:
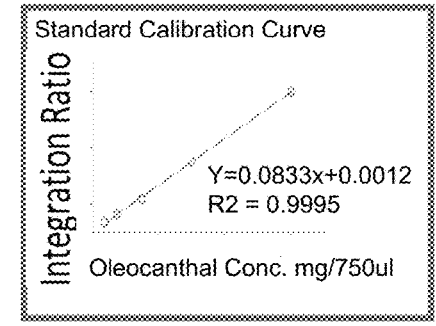

The OC-rich residue, obtained according to previous extraction procedure, was dissolved in CDCl$_3$ (750 µL) and an accurately measured volume of the solution (550 µL) was transferred to the 5 mm NMR tube. $^1$H and $^{13}$C NMR spectra were recorded using tetramethylsilane (TMS) as an internal standard, on a JEOL Eclipse-ECS NMR spectrometer operating at 400 MHz for $^1$H NMR and 100 MHz for $^{13}$C NMR. Typically, 50 scans were collected into 32K data points over a spectral width of 0-16 ppm with a relaxation delay of 1 s and an acquisition time of 2.1 min for $^1$H NMR. For quantitative $^1$H NMR analysis, calibration curves were established using known concentrations of pure OC as an external standard (FIGS. 8F-8H). Quantitation was based on the integration ration of the OC's key aldehydic proton signal at 9.23 ppm and residual CHCl$_3$ peak in the CDCl$_3$ at 7.24 ppm. OC used for the calibration curves was freshly prepared.

HPLC Analysis

Oleocanthal identification and quantification was further confirmed using HPLC analysis on a Simadzu HPLC system equipped with UV/Visible variable wavelength detector. Briefly, OC was dissolved in 50% v/v acetonitrile in water as a mobile phase. Samples (20 µL) were then injected into the Eclipse YD5 C18-RP analytical column (4.6 mm×15 cm) which has been pre-heated to 40° C. The flow rate of the mobile phase was 1.0 mL/min and the analytes were simultaneously detected using the UV detector at λ 230 and 254 nm with 2.8 min retention time. Data acquisition and analysis were performed using Lab Solution™ chromatography software. Quantitatively, calibration curves were prepared using known concentrations of pure OC, as an external standard, and calculating the area under the peak (AUC) for each concentration (FIGS. 8E and 8F).

Zeta-Potential and Particle Size Analysis of Self-Emulsified OC

The mean particle size of OC self-assembled structures in water was measured by photon correlation spectroscopy (PCS) using a Nicomp™ 380 ZLS submicron particle size analyzer (Particle Sizing System, Port Richey, Fla.) at 25° C. and 90° laser light scattering. Samples were diluted with DI water to avoid multiple scattering and achieve a scattering intensity of 300 kHz. The volume-weighted mean diameter of the particles was calculated based on Stokes-Einstein law by curve fitting of the correlation function. The Zeta-potential of OC self-assembled structures in water was measured using the same instrument under the Zeta mode.

Short-Term Stability Study

Short-term stability study was conducted by keeping the OC emulsion samples at two different temperatures; either room temperature (RT) or 4° C. After one month, samples were analyzed using HPLC as previously described. In addition, the particle size and Zeta-potential were calculated for the stored samples and compared with those of initial samples prior to storage to assess the stability of OC emulsions under different storage and temperature conditions.

Cell Lines And Culture Conditions

The human breast cancer cell lines were purchased from ATCC (Manassas, Va.). All cancer cell lines were maintained in RPMI-1640 (GIBCO-Invitrogen, NY) supplemented with 10% fetal bovine serum (FBS) (Gemini Bio-Products), 100 U/mL penicillin G, 100 µg/mL streptomycin and 2 mmol/L glutamine. All cells were maintained at 37° C. in a humidified incubator under 5% $CO_2$. A fresh OC emulsion was prepared by vigorous shaking of a known quantity of oleocanthal with water to afford a stock solution of 10 mM concentration for all assays. Working solutions at their final concentrations for each assay were prepared in appropriate culture medium immediately prior to use. The vehicle control was prepared by adding the maximum volume of water, used in preparing oleocanthal treatment concentrations. Pure oleocanthal was used as a positive control at 10 µM dose based on inventors' previous studies.

MTT Proliferation Assay

Briefly, MDA-MB-231, MDA-MB-468, BT474, and MCF-7 cells, in exponential growth, were seeded at a density of 1×104 cells per well (6 wells/group) in 96-well culture plates and maintained in RPMI-1640 media supplemented with 10% FBS and allowed to adhere overnight at 37° C. under 5% $CO_2$ in a humidified incubator. The next day, cells were washed with phosphate buffer saline (PBS), divided into different treatment groups, and then fed serum-free defined RPMI-1640 media containing 0.5% FBS, to maintain the viability of the cells throughout the experiment, and experimental treatments, containing designated concentrations of oleocanthal or vehicle-treated control media, and incubation resumed at 37° C. under 5% $CO_2$ for 48 h. Control and treatment media were then removed, replaced with fresh media, and 50 µL of fresh MTT solution (1 mg $mL^{-1}$) was added to each well and plates were re-incubated for 4 h at 37° C. The color reaction was stopped by removing the media and adding 100 µL DMSO in each well to dissolve the formed formazan crystals. Incubation at 37° C. was resumed for up to 20 min to ensure complete dissolution of crystals. Absorbance was determined at A 570 nm using an ELISA plate microreader (BioTek, Vt, USA). The % cell survival was calculated as follows: % cell survival=(Cell No. treatment/Cell No. vehicle)×100.

In Vivo Studies

Animals

Female athymic nude mice (Foxn1nu/Foxn1+, 4-5 weeks old) were purchased from Harlan (Indianapolis, Ind.). The animals were acclimated to the animal housing facility and maintained under clean room conditions in sterile filter top cages with Alpha-Dri bedding and housed on high efficiency particulate air-filtered ventilated racks at a temperature of 18-25° C., with a relative humidity of 55 to 65% and a 12 h light/dark cycle, for at least one week before the study. The mice had free access to drinking water and pelleted rodent chow (no. 7012, Harlan/Teklad, Madison, Wis.). All animal experiments were approved by the Institutional Animal Care and Use Committee, University of Louisiana at Monroe, and were handled in strict accordance with good animal practice as defined by the NIH guidelines.

Xenograft Model in Athymic Mice

MDA-MB-231/GFP human breast cancer cells were harvested, pelleted by centrifugation at 850×g for 5 minutes, and re-suspended in sterile serum-free DMEM medium (20 µL). Xylazine (1 mL xylazine at 20 mg/mL) was added to 10 mL ketamine at 100 mg/mL to make 11.0 mL at 92 mg/mL of stock. About 1 mL of this solution was diluted with 9 mL sterile normal saline to make a 9.2 mg/mL solution. About 10 mL of this solution/kg was used for anesthesia, which is equivalent to 10 µL/g. Tumor cell suspension (1×106 cells/20 µL) was inoculated subcutaneously into the second mammary gland fat pad just beneath the nipple of each animal after anesthesia to generate orthotropic breast tumors. At 48 h post-inoculation, the mice were randomly divided into two groups: i) the vehicle-treated control group (n=5), ii) the OC emulsion-treated group (n=5). Treatment (7×/week) started 7 days post-inoculation with orally (p.o.) administered vehicle control (water/saline) or freshly prepared 10 mg/kg OC emulsion. The mice were monitored by measuring tumor volume, body weight, and clinical observation. Tumor volume (V) was calculated by $V=L/2\times W^2$, where L was the length and W was the width of tumors. The results are presented as average ±S.E.M. Differences among various treatment groups were determined by the analysis of variance (ANOVA) followed by Dunnett's test using PASW statistics version 18. A difference of $P<0.05$ was considered statistically significant as compared to the vehicle-treated control group.

Recurrence Prevention After Primary Tumor Excision Experiment

Female athymic nude mice used in previous experiment were anesthetized prior to the surgical excision procedure with ip ketamine/xylazine combination (100 mg/kg/15 mg/kg). 15-20 min after administering the anesthetic animal reflexes tested by gently tapping the hind legs with sterile syringe needle and finally their tumors were surgically excised and each wound was closed by one or two stitches. Ketoprofen, 1 mg/kg was used 12 hours before and 12 h after surgery for effective analgesia. Ophthalmic lubricant was used during the surgery to prevent corneal drying. Bupivicaine (0.25%, 1-2 drops), twice daily, was used topically at the excision wound site, local infiltration along surgery site during closure with a maximum dose of 2 mg/kg. OC, vehicle and positive drug control treatments continued as described for each group.

Additional Data

OC inhibited cell viability and COX-2 expression by activation of AMPK-mediated pathways in HT-29 cells, plausibly explaining in part this compound's preventive and chemotherapeutic potential against colon cancer. Known AMPK and caspase-3 inhibitors blocked the ability of OC to inhibit HT-29 cell colony formation. Results from a chorioallantoic membrane assay also showed that OC can inhibit angiogenesis in vivo.

The anti-inflammatory activity of oleocanthal is mediated at least in part through inhibition of macrophage inflammatory protein 1-a (MIP-1α), IL-6 expression and secretion, and 5-lipoxygenase. Oleocanthal showed a potent HSP90 inhibitory activity, an essential molecular chaperone involved in various cancer hallmarks; OC inhibited ATPase activity and changed HSP90 oligomerization state, promoting the loss of HSP90 molecular chaperone function.

Oleocanthal induced both primary necrotic and apoptotic cell death through enhancement of lysosomal membrane permeabilization (LMP) by inhibiting acid sphingomyelinase activity, which destabilizes the interaction between proteins necessary for lysosomal membrane stability. The cancerous cells were found to have much greater fragility to oleocanthal-induced LMP than normal cells.

Studies conducted by the inventors identified oleocanthal as a c-Met ATP competitive inhibitor. In accord with this finding, oleocanthal selectively inhibited the proliferation of cells of several human breast and prostate cancer lines, without adversely affecting non-tumorigenic human mammary epithelial cells. Our studies demonstrated that oleocanthal inhibited cell proliferation of several human breast cancer lines in vitro and in vivo. The inventors are also aware of the activity of oleocanthal as mTOR inhibitor. Oleocanthal shares nine out of ten critical binding interactions with a potent dual PIK3-y/mTOR natural inhibitor. Oleocanthal inhibites the enzymatic activity of mTOR, with an $IC_{50}$ value of 708 nm. Oleocanthal causes a marked downregulation of phosphorylated mTOR in the TNBC cells MDA-MB-231. It is very likely this is a downstream effect due to oleocanthal's c-Met inhibition. Chemical proteomics proved HSP70 and HSP90, as major oleocanthal interactors in living systems.

In addition to its anticancer activity, oleocanthal has demonstrated an anti-Alzheimer's activity. Oleocanthal enhances the clearance of the Alzheimer disease neurodegenerative hallmark amyloid-beta (Aβ) from the brain via up-regulation of Aβ transport proteins in vitro and in vivo. These findings provide evidence for the potential of oleocanthal to reduce the risk of Alzheimer disease, which will make oleocanthal based product a very popular even for normal healthy individuals for preventive and improved health purposes.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

We claim:
1. A method for extracting S (-)-oleocanthal from olive oil comprising:
    (a) mixing a first volume of water with a second volume of olive oil to form an olive oil/water mixture;
    (b) letting the olive oil/water mixture stand for a period of time sufficient for phase separation;
    (c) removing an aqueous fraction from the olive oil/water mixture of step (b), thereby leaving an olive oil fraction containing a reduced amount of S (-)-oleocanthal; and
    (d) filtering the aqueous fraction to obtain a purified aqueous solution of S (-)-oleocanthal.
2. The method of claim 1 further comprising the step of separating the water from the filtered aqueous S (-)-oleocanthal solution to obtain a dry S (-)-oleocanthal residue.
3. The method of claim 2 further comprising the step of stable freezing under nitrogen the dry S (-)-Oleocanthal residue.
4. The method of claim 1 wherein the olive oil is extra virgin olive oil.
5. The method of claim 1 where the mixing of the volume of water with the volume of olive oil is via vigorous shaking or agitating.
6. The method of claim 1 wherein a total amount of water mixed with the olive oil is at least three times the second volume of olive oil.
7. The method of claim 1 further comprising the step of ultra freezing the aqueous fraction after removal from the olive oil/water mixture.
8. The method of claim 1 wherein the water is separated from the aqueous fraction by freeze drying.
9. The method of claim 1 wherein the water is separated from the aqueous fraction by passing the aqueous fraction over a resin, entrapping the S (-)-oleocanthal, and then eluting the S (-)-oleocanthal from the resin.
10. The method of claim 9 wherein the resin is one of a macroporous styrenic polymeric bead resin allowing for adsorption/desorption process scale applications and having a matrix that provides an aromatic non-polar surface.
11. The method of claim 9 further comprising the steps of washing the resin with water and eluting with acetone.
12. The method of claim 11 further comprising the step of collecting a first portion of acetone elution separate from a second portion of acetone elution, where the first portion of acetone elution is a volume between 15% and 25% of the second portion of acetone elution.
13. The method of claim 1 further comprising performing size exclusion chromatography to obtain a chromatographically purified S (-)-oleocanthal.

14. The method of claim 13 wherein said performing size exclusion chromatography comprises providing $CH_2Cl_2$ an isocratic eluent.

15. The method of claim 1 further comprising the steps of:
   (e) mixing a second volume of water with a volume of the remaining S (-)-oleocanthal reduced olive oil fraction of step (c), to form a second olive oil/water mixture;
   (f) letting the second olive oil/water mixture stand for a period of time sufficient for phase separation;
   (g) removing an aqueous fraction from the second olive oil/water mixture of step (f), thereby leaving an olive oil fraction further reduced in S (-)-oleocanthal; and
   (h) adding the further aqueous fraction of step (g) to the aqueous fraction of steps (c) or (d).

16. The method of claim 15 further comprising the steps of:
   (i) mixing a third volume of water with a volume of the remaining S (-)-oleocanthal reduced containing olive oil fraction of step (g) to form a third further olive oil/water mixture;
   (j) letting the third olive oil/water mixture stand for a period of time sufficient for phase separation;
   (k) removing an aqueous fraction from the third olive oil/water mixture of step (j), thereby leaving an olive oil fraction further reduced in S (-)-oleocanthal; and
   (l) adding the aqueous fraction of step (k) to the aqueous fraction of steps (c) or (d).

17. The method of claim 1 further comprising the steps of:
   (e) separating the water from the aqueous fraction by mixing the aqueous fraction with a non-hexane organic solvent to form an aqueous fraction solvent mixture,
   (f) letting the mixture of step (e) stand for a period of time to sufficient for phase separation,
   (g) evaporating an organic phase of the mixture of step (e) to obtain dry S-oleocanthal residue.

18. The method of claim 1, wherein hexane is not used to remove S (-)-oleocanthal from the olive oil.

* * * * *